(12) United States Patent
Lazarev et al.

(10) Patent No.: US 9,458,190 B2
(45) Date of Patent: Oct. 4, 2016

(54) EXTRACTION AND PARTITIONING OF MOLECULES

(75) Inventors: Alexander Lazarev, Lexington, MA (US); Vera Gross, Newtonville, MA (US)

(73) Assignee: Pressure BioSciences, Inc., South Easton, MA (US)

( * ) Notice: Subject to any disclaimer, the term of this patent is extended or adjusted under 35 U.S.C. 154(b) by 1129 days.

(21) Appl. No.: 12/131,604

(22) Filed: Jun. 2, 2008

(65) Prior Publication Data
US 2008/0300386 A1    Dec. 4, 2008

Related U.S. Application Data

(60) Provisional application No. 60/933,209, filed on Jun. 4, 2007, provisional application No. 60/972,971, filed on Sep. 17, 2007.

(51) Int. Cl.
*C07K 1/14*    (2006.01)

(52) U.S. Cl.
CPC .................................. *C07K 1/145* (2013.01)

(58) Field of Classification Search
None
See application file for complete search history.

(56) References Cited

U.S. PATENT DOCUMENTS

| | | | |
|---|---|---|---|
| 3,556,414 A | 1/1971 | Eberly | |
| 4,544,567 A | 10/1985 | Gottesman | |
| 4,770,780 A | 9/1988 | Moses | |
| 6,120,985 A | 9/2000 | Laugharn, Jr. et al. | |
| 6,150,172 A | 11/2000 | Schmerr et al. | |
| 6,270,723 B1 | 8/2001 | Laugharn, Jr. et al. | |
| 6,274,726 B1 | 8/2001 | Laugharn, Jr. et al. | |
| 6,428,984 B1 | 8/2002 | Pointek et al. | |
| 6,696,019 B2 | 2/2004 | Laugharn, Jr. et al. | |
| 7,064,192 B2 | 6/2006 | Randolph et al. | |
| 7,195,766 B2 | 3/2007 | White | |
| 2002/0137157 A1 | 9/2002 | Randolph et al. | |
| 2002/0197631 A1 | 12/2002 | Lawrence et al. | |
| 2003/0083475 A1 | 5/2003 | Randolph et al. | |
| 2004/0038333 A1 | 2/2004 | Randolph et al. | |
| 2004/0224344 A1* | 11/2004 | Han et al. | 435/6 |
| 2005/0153381 A1 | 7/2005 | Marusich et al. | |
| 2006/0188970 A1 | 8/2006 | Randolph et al. | |

FOREIGN PATENT DOCUMENTS

| | | |
|---|---|---|
| JP | 2002195702 A | 7/2002 |
| WO | 00/65065 A1 | 11/2000 |
| WO | 02/088296 A1 | 11/2002 |
| WO | 2005/117575 A1 | 12/2005 |
| WO | 2008/151136 A1 | 12/2008 |

OTHER PUBLICATIONS

Bera et al., A Novel Azeotropic Mixture for Solvent Extraction of Edible Oils; Agricultural Engineering International: the CiGR Ejournal; Manuscript FP 02 005, vol. VIII (Apr. 2006).
Issac et al., Brian Lipid Composition in Postnatal Iron-Induced Motor Behavior Alterations Following Chronic Neuroleptic Administration in Mice; FEBS Journal, 273: 2232-2243 (2006).
Saad et al., Extraction of Genomic DNA from Filamentous Fungi in Biofilms on Water-Based Paint Coatings; Intl. Biodeterioration & Biodegradation 54: 99-103 (2004).
Bichon E et al., "LC-ESI-MS/MS determination of phenylurea and triazine herbicides and their dealkylated degradation products in oysters", Journal of Chromatography B: Biomedical Sciences & Applications, Elsevier, Amsterdam, NL, vol. 838, No. 2, Jul. 11, 2006, pp. 96-106, XP027981984.
Extend European Search Report for European Application No. 08769978.1 dated Nov. 18, 2011.
Wang Y et al.: "Porcine pulmonary surfactant preparations contain the antibacterial peptide prophenin and a C-terminal 18-residue fragment thereof", Febs Letters, Elseiver, Amsterdam, NL, vol. 460, No. 2, Oct. 29, 1999, pp. 257-262, XP004498691.
Australian Office Action for related application PCT/US2008/065541, dated Nov. 18, 2011.
Ennaceur, et al., "Micellar Aggregates Formed Following the Addition of Hexafluoroisopropanol to Phospholipid Membranes", Langmuir 21:552-561 (2005).
Extended Supplemental European Search Report for European Patent No. EP 09 74 3681 dated Jan. 17, 2012.
Frezza et al: 'Organelle isolation: functional mitochondria from mouse liver, muscle and cultured filroblasts' Nature Protocols vol. 2, No. 2, Feb. 1, 2007, pp. 287-295, XP055038328 ISSN: 1750-2799.
International Search Report from International Application Serial No. PCT/US09/043168 mailed Aug. 18, 2009.
Kristian T et al: "Isolation of mitchondria with high respirtory control from primary cultures of neurons and astrocytes using nitrogen cavitation", Journal of Neuroscience Methods, Elsevier Science Publisher B.V., Amsterdam, NL, vol. 152, No. 1-2, Apr. 15, 2006, pp. 163-143, XP024996899, ISSN: 0165-0270, DOI: 10.1016/ JNEUMETH.2005.08.018 [retrieved on Apr. 15, 2006].
Murata N et al: "Preparation of Girdle Lamella Containing Chloroplasts From the Diatom Phaeodactylum-Tricornutum", Plant and Cell Physiology, vol. 20, No. 6, 1979, pp. 1047-1054, XP009162841, ISSN: 0032-0781.
Patemoste et al., "Partition coefficient of a surfactant between aggregates and solution: application to the micelle-vesicle transition of egg phosphatidylcholine and octyl beta-D-glucopyranoside." Biophys. J. 69:2476-2488 (1995).
Smejkal G B et al: Sample preparation for two-dimensional gel electrophoresis using pressure cycling technology: Analytical Biochemistry, Academic Press Inc, New York, vol. 363, No. 2 Apr. 15, 2007, pp. 309-311, XP025611974, ISSN: 003-2697, DOI: 10.1016/J.AB.2007.01.033 [retrieved on Mar. 21, 2007].
Smejkal Gary B et al: "Increased protein yields from *Escherichia coli* using pressure-cycling technology." Journal of Biomolecular Techniques : JBT Apr. 2006 LNKD-PUBMED: 16741245, vol. 17, No. 2, Apr. 2006, pp. 173-175, XP005015775, ISSN: 1524-0215.
Vial C et al: "Characterization of Fractions Derived From Pig Heart Mitochondria Prepared by French Press and Digitonin Methods", Biology of the Cell (Paris), vol. 41, No. 3, 1981, pp. 195-202, XP009162842, ISSN: 0248-4900.
Written Opinion from International Application Serial No. PCT/US09/043168 mailed Aug. 18, 2009.
Garcia-Manyes, et al., "Effect of Temperature on the Nanomechanics of Lipid Bilayers Studied by Force Spectroscopy", Biophysical Journal, vol. 89, Issue 6, 4261-4274, (Dec. 1, 2005).

\* cited by examiner

*Primary Examiner* — Suzanne M Noakes
*Assistant Examiner* — Jae W Lee
(74) *Attorney, Agent, or Firm* — Lando & Anastasi, LLP

(57) ABSTRACT

Methods of extracting a component of interest from a plurality of components are described.

24 Claims, 5 Drawing Sheets

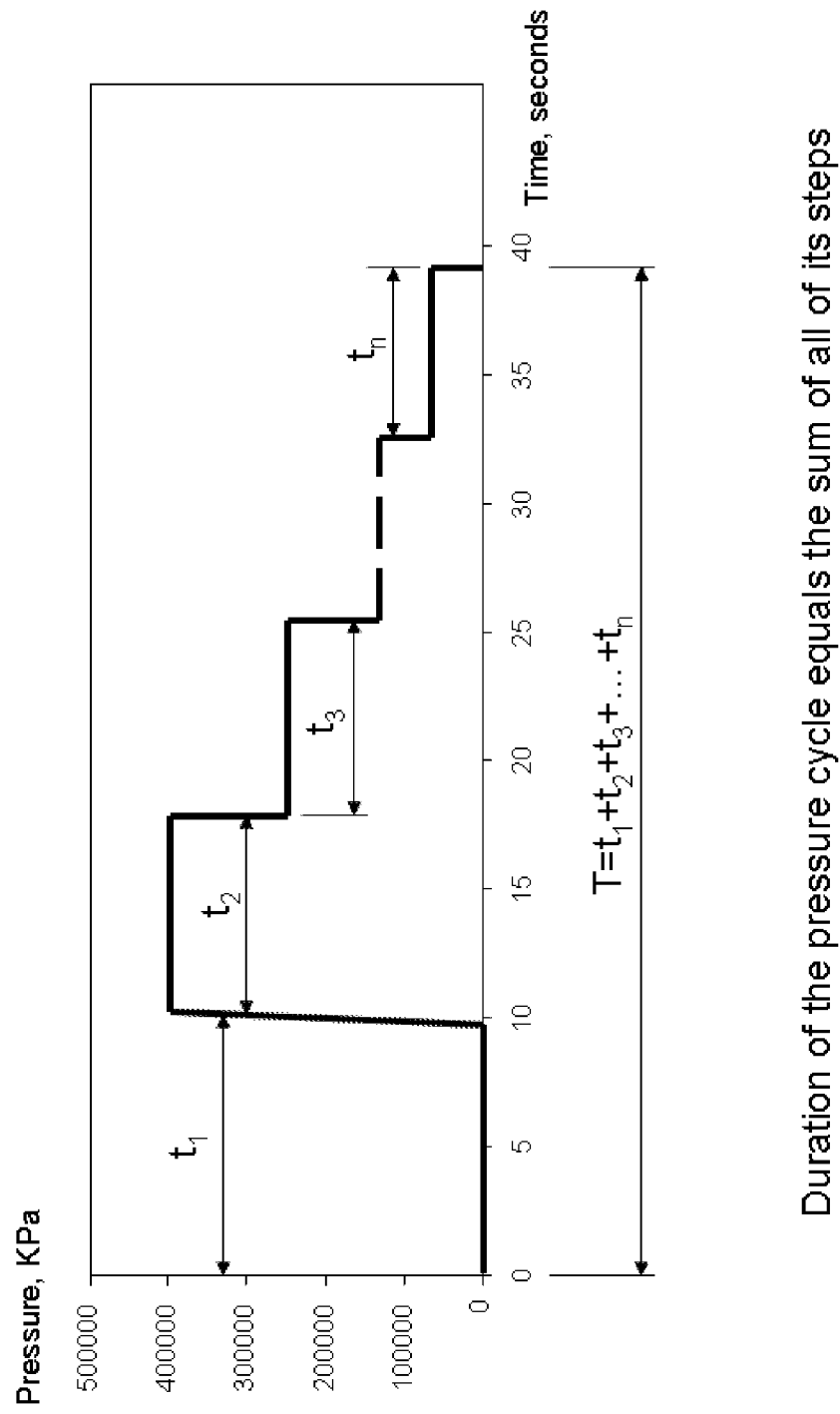

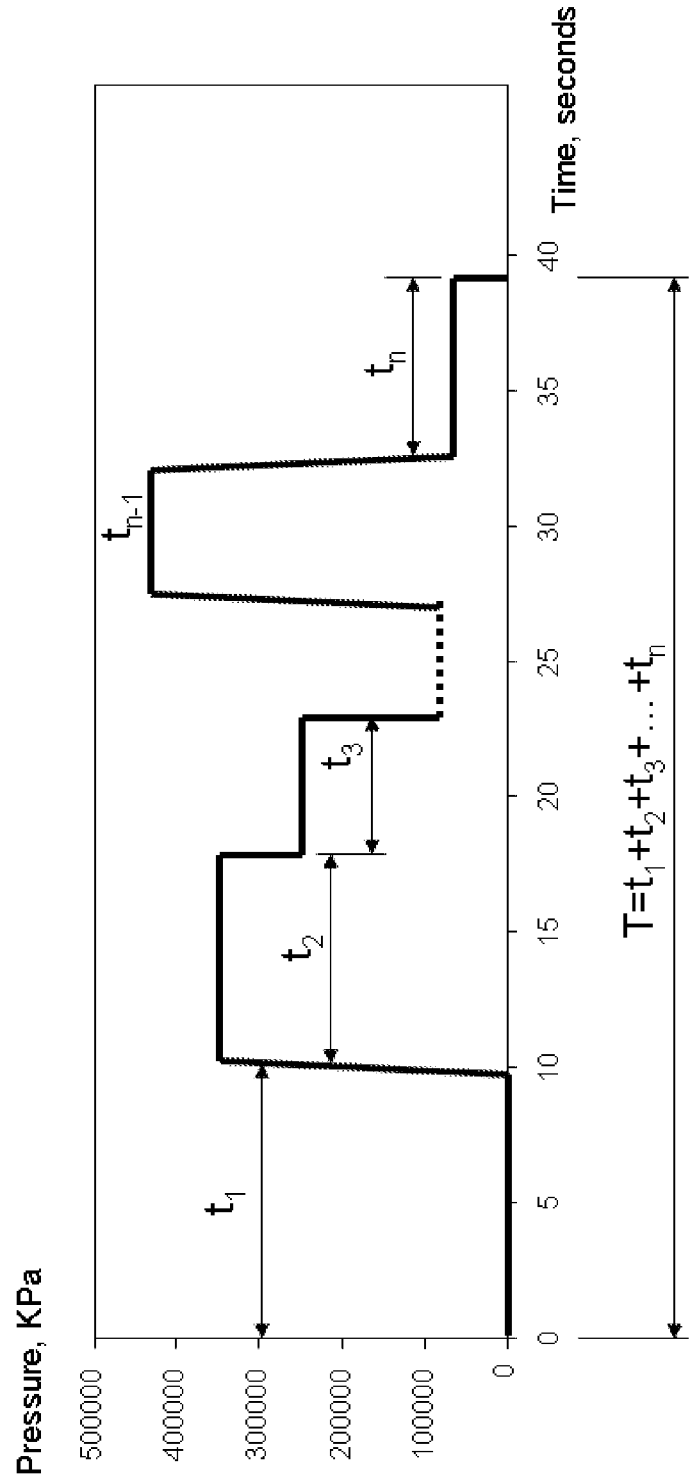

EXTRACTION AND PARTITIONING OF MOLECULES

CROSS REFERENCE TO RELATED APPLICATIONS

This application claims priority to U.S. Ser. No. 60/933,209, filed on Jun. 4, 2007 and U.S. Ser. No. 60/972,971 filed on Sep. 17, 2007. The contents of the aforementioned applications are hereby incorporated by reference in their entirety.

BACKGROUND

Current extraction methods are often specific for a certain class of molecule, to the exclusion and loss of other classes of molecules. Often, a sample to be analyzed is limited in size, and extraction of one type of molecule exhausts the sample or prevents the extraction of additional classes of molecules from the sample. Liquid-liquid partitioning has been employed for extraction of molecular entities from complex mixtures based on the differential solubility of the molecules in different solvents. However, when immiscible or partially miscible solvents are used for liquid-liquid partitioning, the exchange between the solvents occurs only on the solvent interface, while the bulk of the solvents remaining isolated from interaction with each other. Partitioning of molecules between solvents, therefore, requires vigorous mechanical shaking to maintain a large liquid-liquid surface interface area between the solvents. Shaking of the solvents is typically conducted in separatory funnels and is performed with an excess of gas present in the funnel to facilitate the emulsification by shaking. Extracted molecules may be subject to air oxidation or otherwise affected by the presence of a gas phase, e.g., lather formation in the presence of detergents, therefore, rendering conventional liquid-liquid extraction process inconvenient, inefficient, or impossible.

SUMMARY

The present disclosure provides, inter alia, extraction methods that allow an entity (e.g., component) or multiple classes of molecular entities (e.g., components) to be extracted from a sample (e.g., mixture or plurality of components) by employing mixtures of immiscible extraction solvents (e.g., liquid phases or solvent phases), which can possess distinctly different affinities to various classes of sample-derived components. The methods can be used, e.g., for liquid-liquid extraction, gel-liquid extraction, suspension-liquid extraction. In some embodiments, pressure (e.g., a pressure cycle) can be used in the extraction methods. In some embodiments, a heteroazeotrope is present and mutual azeotropic solubility of the solvents is altered by application of increased pressure (e.g., hydrostatic pressure) to the sample, e.g., in an extraction chamber that contains one or more extraction solvent and the sample. High pressure can directly affect micelles by decreasing their size or disrupting them (see, e.g., Ennaceur and Sanderson, *Langmuir* 21:552-561 (2005). Cycles of pressure (e.g., hydrostatic pressure), for example, from ambient to high pressure and then reducing the pressure (e.g., back down to ambient pressure) (pressure cycling), can disrupt cells and tissues more efficiently than non-cycling application of pressure (see, e.g., U.S. Pat. Nos. 6,274,726; 6,120,985; 6,270,723; and 6,696,019).

As used herein, the terms "extraction" and "extracting" refer to the enhancement of one component (e.g., a component of interest) over other components (e.g., contaminants) in one phase (e.g., one phase of a plurality of liquid phases). In some embodiments, the extraction is not a complete extraction, but a partial extraction, enhancing a relative amount of one component (e.g., a component of interest) over another without completely removing and/or isolating the one component relative to the other component(s) (e.g., contaminants) (e.g., about 10%, about 20%, about 30%, about 40%, about 50%, about 60%, about 70%, about 80%, about 85%, about 90%, about 95%, about 96%, about 97%, about 98%, or about 99% of the one component is isolated from the other component(s)). In some embodiments, the one component is completely extracted from the other components (e.g., is completely separated from the other components).

In some aspects, pressure cycling can be used to disrupt or reduce the number of micelles and/or emulsions that are formed during extraction of molecular entities, e.g., from membranes, cells, tissues, and complex matrices, particularly when surfactants or detergents are used to assist in the solubilization of hydrophobic entities in aqueous extraction solvents. Repeated application of pressure (e.g., hydrostatic pressure) can lead to the disruption of micelles and emulsions and to the partitioning of the sample-derived molecules into separate liquid phases, based on their physiochemical properties.

Further, the disclosure describes the use of solvents (e.g., one or more solvents) to enhance the partitioning of sample-derived molecular entities among the solvents, and the solvents have poor mutual solubility at ambient pressure (e.g., chloroform is soluble in water at 0.815% w:w, hexane is soluble in water only at 0.001% w:w) and room temperature (e.g., about 25° C.). High pressure can alter the mutual solubility of solvents. By selecting appropriate solvents, amounts of the solvents and pressure levels, it is possible to transiently mix immiscible solvents and the sample being extracted, which leads to the formation of a metastable mixture, where the resulting soluble solvents possess altered properties, e.g., the ability to dissolve the sample components. Depressurization (e.g., rapid depressurization) of such metastable system results in the separation of the mixture into distinct fractions and partitioning of molecular entities between the solvents according to each of their respective physiochemical properties such as the partitioning coefficient, logP or the distribution coefficient, logD, when partially dissociated compounds are being partitioned (see, e.g., Paternoste et al., *Biophys. J.* 69:2476-2488 (1995) and references cited therein). In some embodiments, use of detergents can be greatly reduced or avoided by using several solvents during extraction.

Furthermore, the disclosure describes the use of ternary and higher mixtures of solvents, where two or more immiscible solvents are augmented with an amphiphilic solvent (e.g., the solvent) are miscible to a greater extent than with either of the otherwise immiscible liquid phases, e.g., water and oil. The presence of an amphiphilic solvent further enhances the ability of increased (e.g., high) pressure to alter mutual solubility of solvents within one another and to promote partitioning of the components of the sample (e.g., mixture) being extracted into distinct phases upon decreasing the pressure to a lower level. Amphiphilic solvents may form stable associations with aqueous phases (by virtue of hydrogen bonding) as well as with oils and lipids by means of hydrophobic interactions. Thus, in certain embodiments, the dissolution of the multi-component sample in the amphiphilic solvent promoted by pressure cycling will result in a phase separation of lipophilic and hydrophilic compounds into two or more liquid phases which can be subsequently mechanically separated.

In one aspect, the disclosure features a method of extracting a component of interest from a plurality of components. The method includes
  providing a sample (e.g., mixture) that contains a plurality of components and at least one liquid phase (e.g., a plurality of liquid phases, e.g., at least two liquid phases) (e.g., forming immiscible liquid phases), wherein the sample (e.g., mixture) is at a first hydrostatic pressure;
  exposing the sample (e.g., mixture) to a second hydrostatic pressure, wherein the second hydrostatic pressure is greater than the first hydrostatic pressure, resulting in the formation of an additional liquid phase;
  reducing the pressure from the second hydrostatic pressure, thereby extracting the component of interest from the plurality of components (e.g., increasing the percentage (or proportion) of the component of interest in one of the liquid phases).

In some embodiments, the plurality of components includes components of varied hydrophobicities.

In some embodiments, the plurality of components includes (e.g., provides) a phase of the plurality of liquid phases.

In some embodiments, a liquid phase forms a solid phase during or upon completion of the extracting.

In some embodiments, a component of the plurality of components is soluble in a liquid phase of the plurality of liquid phases.

In some embodiments, a component of the plurality of components is insoluble in a liquid phase of the plurality of liquid phases.

In some embodiments, the plurality of components includes a colloid. As used herein, a colloid or colloidal dispersion is a heterogeneous mixture that visually appears to be a homogeneous solution. A heterogeneous mixture is a mixture of two phases whereas a solution is one phase. In a colloid, the dispersed phase is made of tiny particles or droplets that are distributed evenly throughout the continuous phase. Examples of colloids include milk, cream, aerosols (e.g., fog, smog, smoke), asphalt, inks, paints, glues, and sea foam.

In some embodiments, the plurality of components comprises an emulsion. As used herein, an emulsion is a type of colloid. An emulsion is a mixture of two immiscible substances. One substance (the dispersed phase) is dispersed in the other (the continuous phase). Examples of emulsions include butter, margarine, espresso, mayonnaise, the photosensitive side of photographic film, cutting fluid for metalworking, paints, inks, lubricants, topical medications, lotions, cosmetic preparations, etc. In butter and margarine, a continuous liquid phase surrounds droplets of water (water-in-oil emulsion).

In some embodiments, the at least two liquid phases are not miscible at the first hydrostatic pressure.

In some embodiments, the at least two liquid phases are miscible (e.g., fully miscible) at the second hydrostatic pressure.

In some embodiments, the at least two liquid phases are not soluble at the first hydrostatic pressure.

In some embodiments, the at least two liquid phases are partially soluble at the first hydrostatic pressure.

In some embodiments, the at least two liquid phases are partially soluble at the second hydrostatic pressure.

In some embodiments, the at least two liquid phases are fully soluble at the second hydrostatic pressure.

In some embodiments, the second hydrostatic pressure is reduced to a third hydrostatic pressure that is the equal to the first hydrostatic pressure. In some embodiments, the sample (e.g., mixture) is exposed to a fourth pressure, wherein the fourth pressure is greater than the first, second, or third pressures.

In some embodiments, the second hydrostatic pressure is reduced to a third hydrostatic pressure that is the greater than the first hydrostatic pressure. In some embodiments, the sample (e.g., mixture) is exposed to a fourth pressure, wherein the fourth pressure is greater than the first, second, or third pressures.

In some embodiments, the second hydrostatic pressure is reduced to a third hydrostatic pressure that is the less than the first hydrostatic pressure. In some embodiments, the sample (e.g., mixture) is exposed to a fourth pressure, wherein the fourth pressure is greater than the first, second, or third pressures.

In some embodiments, reducing the pressure from the second hydrostatic pressure results in the separation of the at least two liquid phases into separate phases and the component of interest is partitioned into one of the at least two liquid phases.

In some embodiments, the sample (e.g., mixture) is exposed to a third pressure and a fourth pressure, wherein the fourth pressure is greater than the first, second, or third pressure.

In some embodiments, the sample (e.g., mixture) contains a secondary container that comprises a reagent. In some embodiments, exposure to the second, third, or fourth hydrostatic pressure causes the secondary container to release its contents, thereby introducing the reagent into the sample (e.g., mixture).

In some embodiments, the plurality of components is partitioned into a liquid phase that does not include the component of interest, e.g., that is substantially free of the component of interest.

In some embodiments, the method further includes isolating/purifying the component of interest from the liquid phase.

In some embodiments, the liquid phases are separated as fractions.

In some embodiments, the extracted component of interest is directly compatible with a downstream process (e.g., analytical method, e.g., HPLC or LC/MS).

In some embodiments, the component of interest is a protein (e.g., membrane bound protein, transmembrane protein, type I or type II membrane protein, receptor, enzyme, a lipoprotein, a glycoprotein). In some embodiments, the conformation of the protein is changed during (or by the completion of) the extraction.

In some embodiments, the component of interest is a polysaccharide (e.g., heparin or heparin-derived polysaccharide), a polyphenol (e.g., a tannin, a phenylpropanoid (e.g., a lignin, a flavonoid), a vitamin, a toxin, a pollutant, a lipid (e.g., phospholipids (e.g., phosphatidylcholine (PtdCho), phosphatidylethanolamine (PtdEtn), phosphatidylinositol (PtdIns), phosphatidylserine (PtdSer)), glycolipids, steroids (e.g., estrogen, progesterone, androgen, testosterone, ecdysteroids such as ecdysterone, corticosteroids such as glucocorticoids and mineralocorticoids, anabolic steroids, cholesterol, phytosterols, brassinosteroids, ergosterols), a membrane (cell membrane, organelle membrane, lipid bilayer), a component present in a bacterial inclusion body, an antigen (e.g., from a bacterium), a virus (e.g., for vaccine production), a pharmaceutical agent such as a small molecule, a metabolite (e.g., a small molecule metabolite), a drug (e.g., a pharmaceutical drug), a drug metabolite, a dye, a food constituent, a nanoparticle formulation, a lipid raft, an amyloid plaque, microtubule, cytosol, or a particular cell type.

In some embodiments, the component of interest is a nucleic acid (DNA (nuclear DNA, mitochondrial DNA), RNA (mRNA, tRNA, rRNA)).

In some embodiments, the component of interest is a virus (e.g., HIV, HPV, hepatitis A, B, C, D, E, F, or G, cytomegalovirus, Epstein-Barr virus, yellow fever, and so forth), or a bacterium (e.g., Gram positive or Gram negative bacteria, mutualist bacteria, pathogenic bacteria).

In some embodiments, the component of interest is a pesticide (e.g., bactericide, fungicide, herbicide, insecticide (e.g., ovicide, larvicide or adulticide), miticide, molluscicide, nematicide, rodenticide, or virucide.

In some embodiments, the component of interest is hydrophobic.

In some embodiments, the component of interest is hydrophilic.

In some embodiments, the component of interest is amphipathic/amphiphilic.

In some embodiments, a plurality of components of interest are extracted from the plurality of components. In some embodiments, the plurality of components of interest contains a nucleic acid and a protein.

In some embodiments, the plurality of components comprises a cell (e.g., prokaryotic or eukaryotic), an organelle (e.g., mitochondrion, nucleus, Golgi apparatus, chloroplast, endoplasmic reticulum, vacuole, acrosome, centriole, cilium, glyoxysome, hydrogenosome, lysosome, melanosome, mitosome, myofibril, nucleolus, parenthesome, peroxisome, ribosome, microsome, vesicle), a membrane, a biological sample (tissue sample (adipose tissue, liver, kidney, skin, pancreas, stomach, intestine, colon, breast, ovary, uterine, prostate, bone, tendon, cartilage, hair, nail, tooth, heart, brain, lung, skin, biopsy, etc.), blood, urine, milk, semen, saliva, mucus, other bodily fluids and solids), collection of cells (e.g., blood, semen, mucus, saliva, tissue biopsy).

In some embodiments, the plurality of components is of biological origin. In some embodiments, the plurality of components of biological origin is from an animal (e.g., mammal (e.g., human or domesticated animal)), reptile, amphibian, fish, insect, avian species, fungus, bacterium, virus, or plant. In some embodiments, the plurality of components of biological origin is from an ancient sample, e.g., fossil (e.g., fossil animal, fossil wood, fossil bone, fossil tooth, fossil dung, etc.).

In some embodiments, the plurality of components includes an emulsion (e.g., latex paint, lubricants, etc.).

In some embodiments, the plurality of components is synthetic/man made (e.g., ink, lubricant, latex paint, cream, lotion, fuel, liquid propellant, elastomer).

In some embodiments, the plurality of components is exposed to a pressure cycle, wherein the first, second, and third hydrostatic pressures are parts of the pressure cycle.

In some embodiments, the sample (e.g., mixture) is exposed to repeated pressure cycles.

In some embodiments, the sample (e.g., mixture) is exposed to between about 1 and about 1000 pressure cycles.

In some embodiments, the sample (e.g., mixture) is exposed to a third hydrostatic pressure wherein the third hydrostatic pressure is less than the first hydrostatic pressure.

In some embodiments, the sample (e.g., mixture) is exposed to a third hydrostatic wherein the third hydrostatic pressure is equal to the first hydrostatic pressure.

In some embodiments, the sample (e.g., mixture) is exposed to a third hydrostatic wherein the third hydrostatic pressure is greater than the first hydrostatic pressure.

In some embodiments, the first hydrostatic pressure is between about $1.33 \times 10^{-7}$ MPa to about 1,000 MPa.

In some embodiments, the first hydrostatic pressure is between about 0.1 MPa to about 1,000 MPa.

In some embodiments, the second hydrostatic pressure is up to about 1,000 MPa.

In some embodiments, the second hydrostatic pressure is between about 100 kPa and about 1,000 MPa.

In some embodiments, the second hydrostatic pressure is between about 133 kPa and about 1,000 MPa.

In some embodiments, the difference in pressure between the first and second hydrostatic pressures is between about 10 kPa to 1 GPa.

In some embodiments, the method is carried out at a temperature between about −40° C. and about +100° C. (e.g., −2° C., 25° C., 70° C.).

In some embodiments, the pressure is hydraulic or pneumatic pressure.

In some embodiments, the plurality of liquid phases comprises an azeotrope.

In some embodiments, the plurality of liquid phases comprises a mixture of various liquids in various specific proportions.

In some embodiments, the plurality of liquid phases is biphasic.

In some embodiments, the plurality of liquid phases is triphasic.

In some embodiments, the plurality of liquid phases includes an aqueous solvent (e.g., water or aqueous solution of buffering compounds and/or salts, such as phosphate buffer, phosphate buffer/saline, Tris buffer, MES buffer, HEPES buffer, ammonium bicarbonate, etc.).

In some embodiments, the plurality of liquid phases includes an organic solvent, (a carbon-containing solvent) (e.g., acetic acid, acetone, acetonitrile, isopropanol, t-butyl alcohol, methylene chloride, or methanol).

In some embodiments, the plurality of liquid phases includes an inorganic nonaqueous solvent which is a solvent other than water, that is not an organic solvent (e.g., liquid ammonia, liquid sulfur dioxide, sulfuryl chloride, sulfuryl chloride fluoride, phosphoryl chloride, dinitrogen tetroxide, antimony trichloride, bromine pentafluoride, hydrogen fluoride, pure sulfuric acid, and another inorganic acid).

In some embodiments, the plurality of liquid phases includes chloroform, tetrachloroethylene, methanol, isopropanol, ethanol, another alcohol (e.g., fluorinated alcohol (e.g., 1,1,1,3,3,3-hexafluoro-2-propanol (HFIP), 2,2,2-trifluoroethanol (TFE), 2-fluoroethanol, 2,2,3,3-tetrafluoropropan-1-ol, 1.3-difluoropropan-2-ol)), water, or an aliphatic hydrocarbon (hexane, heptane), acetonitrile, formic acid, trifluoroacetic acid, glycerol, lipids (e.g., triglycerides, phospholipids, sphingolipids, glycolipidsoils), fluorocarbons, other halocarbons, solutions of detergents, buffers, chaotropic salts, and/or mixtures thereof.

In some embodiments, the plurality of liquid phases includes a protic solvent (e.g., water, methanol, ethanol, formic acid, hydrogen fluoride, or ammonia).

In some embodiments, the plurality of liquid phases includes an aprotic solvent (e.g., dimethyl sulfoxide, dimethylformamide, hexamethylphosphorotriamide, or mixtures thereof). In some embodiments, the solvent(s) is removed from the extracted component of interest, e.g., prior to further processing of the component of interest.

In some embodiments, the solvent(s) is removed by evaporation (e.g., at ambient temperature (e.g., about 20 to about 23.5° C.) or at elevated temperature (e.g., a temperature higher than ambient temperature, e.g., about 27° C., about 30° C., about 32° C., about 35° C., or about 37° C., or greater).

In some embodiments, the solvent(s) is removed by precipitating the component of interest (e.g., by the addition of water), e.g., and removing the solvent supernatant and replacing it with a solvent of choice.

In some embodiments, optimized salt concentrations can be used to selectively precipitate desired components of interest and retain undesired components in the supernatant and vice versa. For example, such an approach can be used to deplete a complex sample of highly abundant protein species (e.g., serum albumin, immunoglobulins, etc.) and enrich for the low abundance proteins of biological significance.

In some embodiments, the plurality of components provides a liquid phase or the plurality of liquid phases.

In some embodiments, the liquid phase is a lipid, organic solvent, aqueous buffer, emulsion, or suspension of solid particles.

In some embodiments, the liquid phase is formed from a solid phase under hydrostatic pressure (e.g., one or more of the liquid phases is a component (e.g., ice) which has a melting temperature higher than the temperature of the extraction process (e.g., lower than 0° C.)). Once the sample (e.g., mixture) is pressurized to a predefined level of hydrostatic pressure, a phase transition occurs and the component (e.g., ice) which has a melting temperature higher than the temperature of the extraction process melts, becoming a liquid phase).

In some embodiments, a solid phase is formed from a liquid phase under hydrostatic pressure, e.g., under hydrostatic pressure.

In some embodiments, the method is performed under hypotonic salt concentrations.

In some embodiments, the method is performed under hypertonic salt concentrations.

In some embodiments, the method is performed under isotonic salt concentrations.

In some embodiments, the salt concentration is altered to selectively precipitate a component of interest and/or to maintain a contaminant in solution.

In some embodiments, the salt concentration is altered to selectively precipitate a contaminant and/or to maintain a component of interest in solution.

In some embodiments, the sample (e.g., mixture) includes a detergent (e.g., SDS).

In some embodiments, the sample (e.g., mixture) is free or substantially free of detergents.

In some embodiments, the sample (e.g., mixture) includes mineral oil.

In some embodiments, the sample (e.g., mixture) includes a buffer (e.g., phosphate buffer solution (PBS)).

In some embodiments, a protein is extracted from a biological membrane.

In some embodiments, a protein is extracted from a lipid phase.

An example of the methods described herein is as follows. Using the methods described herein, a protein, a nucleic acid, or a lipid can be extracted from adipose tissue, brain, nerves, butter, cream, and so forth. A constituent can be extracted from an emulsion or suspension of solid particles such as a pharmaceutical or cosmetic formulation (ointment, lotion, cream, shampoo, conditioner, nanoparticle drug formulation, etc.). A constituent can be extracted from a pharmaceutical formulation in a tablet, capsule or gelcap form. A constituent can be extracted from a multi-phase composition such as emulsion or suspension of solid particles (e.g., ink, paint, lacquer, lubricant, fuel, ingredients for chemical synthesis, etc.), suspension of liposomes, membrane vesicles, and so forth. Oils, terpenes and/or other lipophilic compounds can be extracted from plant material. Various compounds (e.g. alkaloids, flavonoids, isoflavons, proanthocyanidins, anthocyanins) can be extracted from plants (e.g., medicinal plants). Food flavor constituents (e.g., capsaicin) can be extracted from food preparations. A lipid-soluble vitamin (e.g., a tocopherol, carotenoid, lycopene, etc.) can be extracted from plant oils or animal fat. Topical drug formulation constituents can be extracted from skin and underlying tissues.

In some embodiments, a component (e.g., a dye) is extracted from paint.

In some embodiments, a component is extracted from soil.

In some embodiments, a component is extracted from suspension of solid particles.

In some embodiments, the plurality of components includes an emulsion.

In some embodiments, the plurality of components includes a lipid or a solution of one or multiple components in lipid or a mixture of lipids.

In some embodiments, the plurality of components further includes a protein, lipoprotein, glycoprotein, glycolipid, steroid, vitamin, drug substance, or drug metabolite. In some embodiments, the plurality of components includes a cell or a single cell organism.

In some embodiments, the method partitions the plurality of components among the plurality of liquid phases, the method includes
  providing a sample (e.g., mixture), wherein the sample (e.g., mixture) comprises the plurality of components and the plurality of liquid phases, wherein the plurality of liquid phases have poor mutual solubility at ambient pressure and the plurality of liquid phases are fractionated;
  exposing the sample (e.g., mixture) to an increase in pressure, wherein the increased pressure increases the mutual solubility of the plurality of liquid phases, thereby mixing the plurality of liquid phases of poor mutual solubility and resulting in the formation of a metastable mixture; and
  decreasing the pressure of the sample (e.g., mixture), thereby decreasing the solubility of the liquid phases and causing separation of the plurality of liquid phases into fractions and resulting in the partitioning of the components among the plurality of liquid phases.

In some embodiments, the plurality of liquid phases have poor mutual solubility at ambient temperature.

In some embodiments, the disclosure provides a method of extracting a component of interest from a plurality of components. The method includes:
  providing a sample (e.g., mixture) that includes a plurality of components and a plurality of liquid phases, wherein the sample (e.g., mixture) is at a first hydrostatic pressure;
  exposing the sample (e.g., mixture) to a second hydrostatic pressure, wherein the second hydrostatic pressure is greater than the first hydrostatic pressure and at least two liquid phases in the plurality of liquid phases become partially miscible, resulting in formation of a mixed liquid phase possessing altered properties and leading to a dissolution of at least one component; and exposing the sample (e.g., mixture) to a third hydrostatic pressure, wherein the third hydrostatic pressure is lower than the second hydrostatic pressure and wherein exposing the sample (e.g., mixture) to the third hydrostatic pressure (e.g., the transition from the first to second to third pressures) results in the separation of the component of interest from the plurality of components, thereby extracting the component of interest from the plurality of components (e.g., increasing the percentage (or proportion) of the component of interest in one of the liquid phases).

In some aspects, the disclosure features a method of extracting a protein(s) of interest from adipose tissue or from another sample with high lipid content. The method includes:

providing a sample (e.g., mixture) that contains a plurality of components and containing a high amount of lipids (such as adipose or brain tissue), and at least one liquid phase (or a multiplicity of liquids) (e.g., forming immiscible liquid phases), wherein the sample (e.g., mixture) is at a first hydrostatic pressure;

exposing the sample (e.g., mixture) to a second hydrostatic pressure, wherein the second hydrostatic pressure is greater than the first hydrostatic pressure, resulting in the complete or partial solvation of liquid phases in each other, thereby resulting in dissolution of the protein(s) of interest. The method can further include:

reducing the pressure from the second hydrostatic pressure, thereby resulting in the formation of additional one or more liquid phase(s), thereby partitioning the plurality of components between the liquid phases, wherein the protein(s) of interest are partitioned into a liquid phase.

In some embodiments, the resulting liquid phases containing the plurality of components are separated as fractions.

In some embodiments, a liquid phase(s) includes a solvent.

In some embodiments, the resulting liquid phase (e.g., organic phase) containing the protein(s) of interest can be analyzed directly or the solvent can be removed for further processing of the liquid phase containing the protein(s) of interest.

In some embodiments, the solvent can be removed by evaporation (e.g., at ambient temperature (e.g., about 20 to about 23.5° C.) or at elevated temperature (e.g., a temperature higher than ambient temperature, e.g., about 27° C., about 30° C., about 32° C., about 35° C., or about 37° C., or greater).

In some embodiments, the solvent can be removed by precipitating the protein(s) of interest, removing the solvent supernatant and replacing it with a solvent of choice.

In some embodiments, optimized salt concentrations can be used to selectively precipitate desired proteins and retain undesired proteins in the supernatant and vice versa. For example, such an approach can be used to deplete a complex sample of highly abundant protein species (e.g., serum albumin, immunoglobulins, etc.) and enrich for the low abundance proteins of biological significance.

Other features of the methods described herein include:

In some embodiments, the disclosure provides a protein extraction method where cyclic pressure is used to facilitate sample dissolution. A sample may contain proteins and/or lipids such as triglycerides, phospholipids, glycolipids, sphingolipids, etc., or other hydrophobic compounds, e.g., fatty acids, aliphatic hydrocarbons, etc.

In some embodiments, a sample may contain one or more proteins.

In some embodiments, a sample may contain one or more lipids.

In some embodiments, a sample may contain or be a piece of adipose tissue.

In some embodiments, a sample may contain or be a brain tissue.

In some embodiments, a sample may contain or be an emulsion, suspension or colloid.

In some embodiments, a sample may contain or be milk, a milk product, tree sap, etc.

In some embodiments, a sample may contain or be paint, an industrial lubricant, a cosmetic, e.g., cream or lotion.

In some embodiments, dissolution is facilitated by cycling pressure.

In some embodiments, dissolution is facilitated by mechanical homogenization.

In some embodiments, dissolution is facilitated by ultrasonic cell disruption.

In some embodiments, dissolution is facilitated by agitation, mixing, impact of glass, ceramic or metal beads, grinding or blending.

In some embodiments, a liquid phase contains or is HFIP, TFE, PFOA, Trichloroethanol, Trifluoroacetic acid or other halogenated alcohol or acid.

In some embodiments, a liquid phase contains or is other organic solvent (e.g., as described herein).

In some embodiments, a liquid phase contains or is water or aqueous buffer (e.g., mixed with an organic solvent).

In some embodiments, a liquid phase contains or is a mixture of several solvents described herein.

In some embodiments, partitioning is done by stationary incubation (e.g., temperature range −20 to +50° C.).

In some embodiments, partitioning is facilitated by centrifugation (e.g., relative centrifugal force: range 1×g (e.g., no spinning) to 40,000×g)).

In some embodiments, partitioning is facilitated by addition of a hydrophobic liquid reagent (e.g., oil, lipid, mineral oil, aliphatic hydrocarbon, etc., or a mixture thereof) to the sample to promote phase separation, if sample-derived hydrophobic material is insufficient to form a layer.

In some embodiments, partitioning is done by any combination of the methods described above.

In some embodiments, sample dissolution occurs, but no partitioning is observed (e.g., too little lipid present).

In some embodiments, at least one liquid phase is formed after sample dissolution.

In some embodiments, liquid phases are physically separated by pipetting, decanting, absorption, etc.

In some embodiments, liquid phases are separated using column chromatography (an example of absorption).

In some embodiments, a sample (polar phase) is diluted to induce precipitation following separation of liquid phases.

In some embodiments, liquid phases are not separated, the sample is instead diluted to induce precipitation.

In another aspect, the disclosure features a method for extracting a component of interest (e.g., protein) from a plurality of components. The method involves exposing a plurality of components to a solvent such as 1,1,1,3,3,3-hexafluoro-2-propanol (HFIP), TFE, PFOA, Trichloroethanol, Trifluoroacetic acid or other halogenated alcohol or acid. Exposure to the solvent can extract the component of interest from the plurality. The method can also include a mechanical step (e.g., homogenization step), e.g., to promote the extraction. As another example, instead of including a mechanical step, the method can include exposing the sample to a change in pressure (e.g., with or without cycling of pressure).

In some embodiments, the method includes
providing a sample (e.g., mixture) that contains a plurality of components and at least one liquid phase (e.g., a plurality of liquid phases), wherein the liquid phase contains a solvent (e.g., HFIP, TFE, PFOA, Trichloroethanol, Trifluoroacetic acid or other halogenated alcohol or acid); and
performing at least one processing step on the sample (e.g., mixture), thereby creating at least two liquid phases and thereby extracting the component of interest from the plurality of components.

In some embodiments, the processing step includes one or more of temperature, microwave radiation, or mechanical processing.

In some embodiments, the mechanical processing step includes one or more of homogenizing (e.g., physical homogenization, e.g., bead beater, sonication, rotor-stator homogenizer, Dounce homogenizer, Potter-homogenizer), vortexing, sonicating, pipetting, shearing (e.g., syringe shearing), grinding (e.g., mortar and pestle grinding), shaking, mixing, blending, hammering, and so forth. In some embodiments, the mechanical processing step includes a mass transfer step (e.g., vigorous mixing, mechanical shaking, or hammering).

In some embodiments, the method includes simultaneous (synergistic) or alternating application of pressure (e.g., pressure cycle(s)) and another type(s) of processing, e.g., temperature, microwave radiation, or mechanical processing (e.g., of one (or more) types of mechanical processing, alone or in combination with pressure or another type of processing), etc.

In some embodiments, the method includes simultaneous (synergistic) or alternating application of two (or more) types of processing, e.g., temperature, microwave radiation, or mechanical processing (e.g., of two (or more) types of mechanical processing, alone or in combination with another type of processing), etc.

In some embodiments, a liquid phase forms a solid phase during or upon completion of the extracting.

In some embodiments, the component of interest is a protein.

In some embodiments, the component of interest is a proteome.

In some embodiments, the plurality of components includes components of varied hydrophobicities.

In some embodiments, the plurality of components includes (e.g., provides) a phase of the plurality of liquid phases.

In some embodiments, a component of the plurality of components is soluble in a liquid phase of the plurality of liquid phases.

In some embodiments, a component of the plurality of components is insoluble in a liquid phase of the plurality of liquid phases.

In some embodiments, the plurality of liquid phases comprises an azeotrope.

In some embodiments, the plurality of liquid phases comprises a mixture of various liquids in various specific proportions.

In some embodiments, the plurality of liquid phases is biphasic.

In some embodiments, the plurality of liquid phases is triphasic.

In some embodiments, the resulting liquid phase (e.g., organic phase) containing the protein(s) of interest can be analyzed directly or the solvent can be removed for further processing of the liquid phase containing the protein(s) of interest.

In some embodiments, the sample (e.g., mixture) includes a detergent (e.g., SDS).

In some embodiments, the sample (e.g., mixture) is free or substantially free of detergents.

In some embodiments, the sample (e.g., mixture) includes mineral oil.

In some embodiments, the sample (e.g., mixture) includes a buffer (e.g., phosphate buffer solution (PBS)).

In some embodiments, a protein is extracted from a biological membrane.

In some embodiments, a protein is extracted from a lipid phase.

In some embodiments, the plurality of components includes a colloid. As used herein, a colloid or colloidal dispersion is a heterogeneous mixture that visually appears to be a homogeneous solution. A heterogeneous mixture is a mixture of two phases whereas a solution is one phase. In a colloid, the dispersed phase is made of tiny particles or droplets that are distributed evenly throughout the continuous phase. Examples of colloids include milk, cream, aerosols (e.g., fog, smog, smoke), asphalt, inks, paints, glues, and sea foam.

In some embodiments, the plurality of components comprises an emulsion. As used herein, an emulsion is a type of colloid. An emulsion is a mixture of two immiscible substances. One substance (the dispersed phase) is dispersed in the other (the continuous phase). Examples of emulsions include butter and margarine, espresso, mayonnaise, the photo-sensitive side of photographic film, cutting fluid for metalworking, paints, inks, lubricants, topical medications, lotions, cosmetic preparations, etc. In butter and margarine, a continuous liquid phase surrounds droplets of water (water-in-oil emulsion).

In some embodiments, the plurality of components is partitioned into a liquid phase that does not include the component of interest, e.g., that is substantially free of the component of interest.

In some embodiments, the method further includes isolating/purifying the component of interest from the liquid phase.

In some embodiments, the liquid phases are separated as fractions.

In some embodiments, the extracted component of interest is directly compatible with a downstream process (e.g., analytical method, e.g., HPLC or LC/MS).

In some embodiments, the component of interest is a protein (e.g., membrane bound protein, transmembrane protein, type I or type II membrane protein, receptor, enzyme, a lipoprotein, a glycoprotein). In some embodiments, the conformation of the protein is changed during (or by the completion of) the extraction.

In some embodiments, the component of interest is a polysaccharide (e.g., heparin or heparin-derived polysaccharide, a polyphenol (e.g., a tannin, a phenylpropanoid (e.g., a lignin, a flavonoid), a vitamin, a toxin, a pollutant, a lipid (e.g., phospholipids (e.g., phosphatidylcholine (PtdCho), phosphatidylethanolamine (PtdEtn), phosphatidylinositol (PtdIns), phosphatidylserine (PtdSer)), glycolipids, steroids (e.g., estrogen, progesterone, androgen, testosterone, ecdysteroids such as ecdysterone, corticosteroids such as glucocorticoids and mineralocorticoids, anabolic steroids, cholesterol, phytosterols, brassinosteroids, ergosterols), a membrane (cell membrane, organelle membrane, lipid bilayer), a component present in a bacterial inclusion body, an antigen (e.g., from a bacterium), a virus (e.g., for vaccine production), a pharmaceutical agent such as a small molecule, a metabolite (e.g., a small molecule metabolite), a drug (e.g., a pharmaceutical drug), a drug metabolite, a dye, a food constituent, a nanoparticle formulation, a lipid raft, an amyloid plaque, microtubule, cytosol, or a particular cell type.

In some embodiments, the component of interest is a nucleic acid (DNA (nuclear DNA, mitochondrial DNA), RNA (mRNA, tRNA, rRNA)).

In some embodiments, the component of interest is a virus (e.g., HIV, HPV, hepatitis A, B, C, D, E, F, or G, cytomegalovirus, Epstein-Barr virus, yellow fever, and so forth), or a bacterium (e.g., Gram positive or Gram negative bacteria, mutualist bacteria, pathogenic bacteria).

In some embodiments, the component of interest is a pesticide (e.g., bactericide, fungicide, herbicide, insecticide (e.g., ovicide, larvicide or adulticide), miticide, molluscicide, nematicide, rodenticide, or virucide.

In some embodiments, the component of interest is hydrophobic.

In some embodiments, the component of interest is hydrophilic.

In some embodiments, the component of interest is amphipathic/amphiphilic.

In some embodiments, a plurality of components of interest are extracted from the plurality of components. In some embodiments, the plurality of components of interest contains a nucleic acid and a protein.

In some embodiments, the plurality of components comprises a cell (e.g., prokaryotic or eukaryotic), an organelle (e.g., mitochondrion, nucleus, Golgi apparatus, chloroplast, endoplasmic reticulum, vacuole, acrosome, centriole, cilium, glyoxysome, hydrogenosome, lysosome, melanosome, mitosome, myofibril, nucleolus, parenthesome, peroxisome, ribosome, microsome, vesicle), a membrane, a biological sample (tissue sample (adipose tissue, liver, kidney, skin, pancreas, stomach, intestine, colon, breast, ovary, uterine, prostate, bone, tendon, cartilage, hair, nail, tooth, heart, brain, lung, skin, biopsy, etc.), blood, urine, milk, semen, saliva, mucus, other bodily fluids and solids), collection of cells (e.g., blood, semen, mucus, saliva, tissue biopsy).

In some embodiments, the plurality of components is of biological origin. In some embodiments, the plurality of components of biological origin is from an animal (e.g., mammal (e.g., human or domesticated animal)), reptile, amphibian, fish, insect, avian species, fungus, bacterium, virus, or plant. In some embodiments, the plurality of components of biological origin is from an ancient sample, e.g., fossil (e.g., fossil animal, fossil wood, fossil bone, fossil tooth, fossil dung, etc.).

In some embodiments, the plurality of components includes an emulsion (e.g., latex paint, lubricants, etc.).

In some embodiments, the plurality of components is synthetic/man made (e.g., ink, lubricant, latex paint, cream, lotion, fuel, liquid propellant, elastomer).

In some embodiments, a component is extracted from suspension of solid particles.

In some embodiments, the plurality of components includes an emulsion.

In some embodiments, the plurality of components includes a lipid or a solution of one or multiple components in lipid or a mixture of lipids.

In some embodiments, the plurality of components further includes a protein, lipoprotein, glycoprotein, glycolipid, steroid, vitamin, drug substance, or drug metabolite. In some embodiments, the plurality of components includes a cell or a single cell organism.

In some embodiments, the solvent(s) is removed from the extracted component of interest, e.g., prior to further processing of the component of interest.

In some embodiments, the solvent(s) is removed by evaporation (e.g., at ambient temperature (e.g., about 20 to about 23.5° C.) or at elevated temperature (e.g., a temperature higher than ambient temperature, e.g., about 27° C., about 30° C., about 32° C., about 35° C., or about 37° C., or greater).

In some embodiments, the solvent(s) is removed by precipitating the component of interest, e.g., and removing the solvent supernatant and replacing it with a solvent of choice.

In some embodiments, optimized salt concentrations can be used to selectively precipitate desired components of interest and retain undesired components in the supernatant and vice versa. For example, such an approach can be used to deplete a complex sample of highly abundant protein species (e.g., serum albumin, immunoglobulins, etc.) and enrich for the low abundance proteins of biological significance.

In some embodiments, the method is carried out at a temperature between about −40° C. and about +100° C. (e.g., −2° C., 25° C., 70° C.).

In some embodiments, the method is performed under hypotonic salt concentrations.

In some embodiments, the method is performed under hypertonic salt concentrations.

In some embodiments, the method is performed under isotonic salt concentrations.

In some embodiments, the salt concentration is altered to selectively precipitate a component of interest and/or to maintain a contaminant in solution.

In some embodiments, the salt concentration is altered to selectively precipitate a contaminant and/or to maintain a component of interest in solution.

In some embodiments, liquid phases are physically separated by pipetting, decanting, absorption, etc.

In some embodiments, liquid phases are separated using column chromatography (an example of absorption).

In some embodiments, a sample (polar phase) is diluted to induce precipitation following separation of liquid phases.

In some embodiments, liquid phases are not separated, sample is instead diluted to induce precipitation.

In some aspects, processing can be used to disrupt or alter micelles and/or emulsions that are formed during extraction of molecular entities, e.g., from membranes, cells, tissues, and complex matrices, particularly when surfactants or detergents are used to assist in the solubilization of hydrophobic entities in aqueous extraction solvents. Application of processing (e.g., repeated application of processing (e.g., mechanical processing)) can lead to the disruption of micelles and emulsions and to the partitioning of the sample-derived molecules into separate liquid phases, based on their physiochemical properties.

In some embodiments, the processing step includes one or more of temperature, microwave radiation, or mechanical processing.

In some embodiments, the mechanical processing step includes one or more of homogenizing (e.g., physical homogenization, e.g., bead beater, sonication, rotor-stator homogenizer, Dounce homogenizer, Potter-homogenizer), vortexing, sonicating, pipetting, shearing (e.g., syringe shearing), grinding (e.g., mortar and pestle grinding), shaking, mixing, blending, hammering, and so forth. In some embodiments, the mechanical processing step includes a mass transfer step (e.g., vigorous mixing, mechanical shaking, or hammering).

In some embodiments, the method includes simultaneous (synergistic) or alternating application of pressure (e.g., pressure cycle(s)) and another type of processing, e.g., temperature, microwave radiation, or mechanical processing etc.

Further, the disclosure describes the use of solvents (e.g., one or more solvents) to enhance the partitioning of sample-derived molecular entities among the solvents, and the solvents have poor mutual solubility at ambient pressure (e.g., chloroform is soluble in water at 0.815% w:w, hexane is soluble in water only at 0.001% w:w) and room temperature (e.g., about 25° C.). Mechanical processing can alter the mutual solubility of solvents. By selecting appropriate solvents, amounts of the solvents and amounts (e.g., duration and/or force) of mechanical processing, it is possible to transiently mix immiscible solvents and the sample being extracted, which leads to the formation of a metastable mixture, where the resulting soluble solvents possess altered properties, e.g., the ability to dissolve the sample components. Cessation or reduction of the mechanical processing of such a metastable system results in the separation of the mixture into distinct fractions and partitioning of molecular entities between the solvents according to each of their respective physiochemical properties such as the partitioning coefficient, logP or the distribution coefficient, logD, when partially dissociated compounds are being partitioned (see, e.g., Paternoste et al., *Biophys. J.* 69:2476-2488 (1995) and references cited therein). In some embodiments, use of detergents can be greatly reduced or avoided by using several solvents during extraction.

Furthermore, the disclosure describes the use of ternary and higher mixtures of solvents, where two or more immiscible solvents are augmented with an amphiphilic solvent (e.g., the solvent) are miscible to a greater extent than with either of the otherwise immiscible liquid phases, e.g., water and oil. The presence of an amphiphilic solvent further enhances the ability of mechanical processing to alter mutual solubility of solvents within one another and to promote partitioning of the components of the sample (e.g., mixture) being extracted into distinct phases upon reducing or ceasing the mechanical processing. Amphiphilic solvents may form stable associations with aqueous phases (by virtue of hydrogen bonding) as well as with oils and lipids by means of hydrophobic interactions. Thus, in certain embodiments, the dissolution of the multi-component sample in the amphiphilic solvent promoted by mechanical processing will result in a phase separation of lipophilic and hydrophilic compounds into two or more liquid phases which can be subsequently mechanically separated.

In one aspect, the disclosure features a method of extracting a component of interest from a plurality of components. The method includes providing a sample (e.g., mixture) that contains a plurality of components and at least one liquid phase (e.g., a plurality of liquid phases) (e.g., forming immiscible liquid phases);

performing a first processing step on the sample (e.g., mixture), resulting in the formation of a suspension, a slurry, an emulsion, micelles, or an additional liquid phase;

decreasing or ceasing the processing step, thereby extracting the component of interest from the plurality of components (e.g., increasing the percentage (or proportion) of the component of interest in one of the liquid phases).

In some embodiments, the processing step includes one or more of temperature, microwave radiation, or mechanical processing.

In some embodiments, the mechanical processing step includes one or more of homogenizing (e.g., physical homogenization, e.g., bead beater, sonication, rotor-stator homogenizer, Dounce homogenizer, Potter-homogenizer), vortexing, sonicating, pipetting, shearing (e.g., syringe shearing), grinding (e.g., mortar and pestle grinding), shaking, mixing, blending, hammering, and so forth. In some embodiments, the mechanical processing step includes a mass transfer step (e.g., vigorous mixing, mechanical shaking, or hammering).

In some embodiments, the method includes simultaneous (synergistic) or alternating application of pressure (e.g., pressure cycle(s)) and another type of processing, e.g., temperature, microwave radiation, or mechanical processing etc.

In one aspect, the disclosure features a method of extracting a component of interest from a plurality of components. The method includes providing a sample (e.g., mixture) that contains a plurality of components and at least one liquid phase (e.g., a plurality of liquid phases) (e.g., forming immiscible liquid phases);

performing a first mechanical processing step on the sample (e.g., mixture), resulting in the formation of a suspension, a slurry, an emulsion, micelles, or an additional liquid phase;

decreasing (reducing) or ceasing the mechanical processing step, thereby extracting the component of interest from the plurality of components (e.g., increasing the percentage (or proportion) of the component of interest in one of the liquid phases).

In some embodiments, the mechanical processing step includes one or more of homogenizing (e.g., physical homogenization, e.g., bead beater, sonication, rotor-stator homogenizer, Dounce homogenizer, Potter-homogenizer), vortexing, sonicating, pipetting, shearing (e.g., syringe shearing), grinding (e.g., mortar and pestle grinding), shaking, mixing, blending, hammering, and so forth. In some embodiments, the mechanical processing step includes a mass transfer step (e.g., vigorous mixing, mechanical shaking, or hammering).

In some embodiments, the method includes simultaneous (synergistic) or alternating application of a mechanical processing step and pressure (e.g., pressure cycle(s)) or another type of processing, e.g., temperature, or microwave radiation, etc.

In some embodiments, the plurality of components includes components of varied hydrophobicities.

In some embodiments, the plurality of components includes (e.g., provides) a phase of the plurality of liquid phases.

In some embodiments, a liquid phase forms a solid phase during or upon completion of the extracting.

In some embodiments, a component of the plurality of components is soluble in a liquid phase of the plurality of liquid phases.

In some embodiments, a component of the plurality of components is insoluble in a liquid phase of the plurality of liquid phases.

In some embodiments, the plurality of components includes a colloid. As used herein, a colloid or colloidal dispersion is a heterogeneous mixture that visually appears to be a homogeneous solution. A heterogeneous mixture is a mixture of two phases whereas a solution is one phase. In a colloid, the dispersed phase is made of tiny particles or droplets that are distributed evenly throughout the continuous phase. Examples of colloids include milk, cream, aerosols (e.g., fog, smog, smoke), asphalt, inks, paints, glues, and sea foam.

In some embodiments, the plurality of components comprises an emulsion. As used herein, an emulsion is a type of colloid. An emulsion is a mixture of two immiscible substances. One substance (the dispersed phase) is dispersed in the other (the continuous phase). Examples of emulsions include butter, margarine, espresso, mayonnaise, the photosensitive side of photographic film, cutting fluid for metalworking, paints, inks, lubricants, topical medications, lotions, cosmetic preparations, etc. In butter and margarine, a continuous liquid phase surrounds droplets of water (water-in-oil emulsion).

In some embodiments, the at least two liquid phases are not miscible prior to the first mechanical processing step.

In some embodiments, the at least two liquid phases are miscible (e.g., fully miscible) after performing a mechanical processing step.

In some embodiments, the at least two liquid phases are not soluble prior to mechanical processing.

In some embodiments, the at least two liquid phases are partially soluble after performing a first mechanical processing step.

In some embodiments, the at least two liquid phases are fully soluble after performing a first mechanical processing step.

In some embodiments, the first mechanical processing step is terminated. In some embodiments, the sample (e.g., mixture) is exposed to a second mechanical processing step, wherein the second mechanical processing step is the same type of mechanical processing as the first mechanical processing step or is a different type of mechanical processing step.

In some embodiments, a second mechanical processing step is performed and is the same type of mechanical processing as the first mechanical processing step or is a different type of mechanical processing step. In some embodiments, the sample (e.g., mixture) is exposed to a third mechanical processing step that is the same type of mechanical processing as the first or second mechanical processing step or is a different type of mechanical processing step than the first or second mechanical processing step.

In some embodiments, decreasing or ceasing the mechanical processing step results in the separation of the at least two liquid phases into separate phases and the component of interest is partitioned into one of the at least two liquid phases.

In some embodiments, the sample (e.g., mixture) comprises a secondary container that comprises a reagent. In some embodiments, exposure to the first, second, or third mechanical processing step causes the secondary container to release its contents, thereby introducing the reagent into the sample (e.g., mixture).

In some embodiments, the plurality of components is partitioned into a liquid phase that does not include the component of interest, e.g., that is substantially free of the component of interest.

In some embodiments, the method further includes isolating/purifying the component of interest from the liquid phase.

In some embodiments, the liquid phases are separated as fractions.

In some embodiments, the extracted component of interest is directly compatible with a downstream process (e.g., analytical method, e.g., HPLC or LC/MS).

In some embodiments, the component of interest is a protein (e.g., membrane bound protein, transmembrane protein, type I or type II membrane protein, receptor, enzyme, a lipoprotein, a glycoprotein). In some embodiments, the conformation of the protein is changed during (or by the completion of) the extraction.

In some embodiments, the component of interest is a polysaccharide (e.g., heparin or heparin-derived polysaccharide), a polyphenol (e.g., a tannin, a phenylpropanoid (e.g., a lignin, a flavonoid), a vitamin, a toxin, a pollutant, a lipid (e.g., phospholipids (e.g., phosphatidylcholine (PtdCho), phosphatidylethanolamine (PtdEtn), phosphatidylinositol (PtdIns), phosphatidylserine (PtdSer)), glycolipids, steroids (e.g., estrogen, progesterone, androgen, testosterone, ecdysteroids such as ecdysterone, corticosteroids such as glucocorticoids and mineralocorticoids, anabolic steroids, cholesterol, phytosterols, brassinosteroids, ergosterols), a membrane (cell membrane, organelle membrane, lipid bilayer), a component present in a bacterial inclusion body, an antigen (e.g., from a bacterium), a virus (e.g., for vaccine production), a pharmaceutical agent such as a small molecule, a metabolite (e.g., a small molecule metabolite), a drug (e.g., a pharmaceutical drug), a drug metabolite, a dye, a food constituent, a nanoparticle formulation, a lipid raft, an amyloid plaque, microtubule, cytosol, or a particular cell type.

In some embodiments, the component of interest is a nucleic acid (DNA (nuclear DNA, mitochondrial DNA), RNA (mRNA, tRNA, rRNA)).

In some embodiments, the component of interest is a virus (e.g., HIV, HPV, hepatitis A, B, C, D, E, F, or G, cytomegalovirus, Epstein-Barr virus, yellow fever, and so forth), or a bacterium (e.g., Gram positive or Gram negative bacteria, mutualist bacteria, pathogenic bacteria).

In some embodiments, the component of interest is a pesticide (e.g., bactericide, fungicide, herbicide, insecticide (e.g., ovicide, larvicide or adulticide), miticide, molluscicide, nematicide, rodenticide, or virucide.

In some embodiments, the component of interest is hydrophobic.

In some embodiments, the component of interest is hydrophilic.

In some embodiments, the component of interest is amphipathic/amphiphilic.

In some embodiments, a plurality of components of interest are extracted from the plurality of components. In some embodiments, the plurality of components of interest contains a nucleic acid and a protein.

In some embodiments, the plurality of components comprises a cell (e.g., prokaryotic or eukaryotic), an organelle (e.g., mitochondrion, nucleus, Golgi apparatus, chloroplast, endoplasmic reticulum, vacuole, acrosome, centriole, cilium, glyoxysome, hydrogenosome, lysosome, melanosome, mitosome, myofibril, nucleolus, parenthesome, peroxisome, ribosome, microsome, vesicle), a membrane, a biological sample (tissue sample (adipose tissue, liver, kidney, skin, pancreas, stomach, intestine, colon, breast, ovary, uterine, prostate, bone, tendon, cartilage, hair, nail, tooth, heart, brain, lung, skin, biopsy, etc.), blood, urine, milk, semen, saliva, mucus, other bodily fluids and solids), collection of cells (e.g., blood, semen, mucus, saliva, tissue biopsy).

In some embodiments, the plurality of components is of biological origin. In some embodiments, the plurality of components of biological origin is from an animal (e.g., mammal (e.g., human or domesticated animal)), reptile, amphibian, fish, insect, avian species, fungus, bacterium, virus, or plant. In some embodiments, the plurality of components of biological origin is from an ancient sample, e.g., fossil (e.g., fossil animal, fossil wood, fossil bone, fossil tooth, fossil dung, etc.).

In some embodiments, the plurality of components includes an emulsion (e.g., latex paint, lubricants, etc.).

In some embodiments, the plurality of components is synthetic/man made (e.g., ink, lubricant, latex paint, cream, lotion, fuel, liquid propellant, elastomer).

In some embodiments, the mechanical processing step is performed on the plurality of components more than once.

In some embodiments, the sample (e.g., mixture) is exposed to repeated mechanical processing steps.

In some embodiments, the sample (e.g., mixture) is exposed to between about 1 and about 1000 mechanical processing steps.

In some embodiments, the same type mechanical processing steps are performed.

In some embodiments, different types of mechanical processing steps are performed. E.g., one or more steps of one or more of the following can be performed: homogenizing (e.g., physical homogenization, e.g., bead beater, sonication, rotor-stator homogenizer, Dounce homogenizer, Potter-homogenizer), vortexing, sonicating, pipetting, shearing (e.g., syringe shearing), grinding (e.g., mortar and pestle grinding), shaking, mixing, blending, and hammering.

In some embodiments, the plurality of liquid phases comprises an azeotrope.

In some embodiments, the plurality of liquid phases comprises a mixture of various liquids in various specific proportions.

In some embodiments, the plurality of liquid phases is biphasic.

In some embodiments, the plurality of liquid phases is triphasic.

In some embodiments, the plurality of liquid phases includes an aqueous solvent (e.g., water or aqueous solution of buffering compounds and/or salts, such as phosphate buffer, phosphate buffer/saline, Tris buffer, MES buffer, HEPES buffer, ammonium bicarbonate, etc.).

In some embodiments, the plurality of liquid phases includes an organic solvent, (a carbon-containing solvent) (e.g., acetic acid, acetone, acetonitrile, isopropanol, t-butyl alcohol, methylene chloride, or methanol).

In some embodiments, the plurality of liquid phases includes an inorganic nonaqueous solvent which is a solvent other than water, that is not an organic solvent (e.g., liquid ammonia, liquid sulfur dioxide, sulfuryl chloride, sulfuryl chloride fluoride, phosphoryl chloride, dinitrogen tetroxide, antimony trichloride, bromine pentafluoride, hydrogen fluoride, pure sulfuric acid, and another inorganic acid).

In some embodiments, the plurality of liquid phases includes chloroform, tetrachloroethylene, methanol, isopropanol, ethanol, another alcohol (e.g., fluorinated alcohol (e.g., 1,1,1,3,3,3-hexafluoro-2-propanol (HFIP), 2,2,2-trifluoroethanol (TFE), 2-fluoroethanol, 2,2,3,3-tetrafluoropropan-1-ol, 1.3-difluoropropan-2-ol)), water, or an aliphatic hydrocarbon (hexane, heptane), acetonitrile, formic acid, trifluoroacetic acid, glycerol, lipids (e.g., triglycerides, phospholipids, sphingolipids, glycolipidsoils), fluorocarbons, other halocarbons, solutions of detergents, buffers, chaotropic salts, and/or mixtures thereof.

In some embodiments, the plurality of liquid phases includes a protic solvent (e.g., water, methanol, ethanol, formic acid, hydrogen fluoride, or ammonia).

In some embodiments, the plurality of liquid phases includes an aprotic solvent (e.g., dimethyl sulfoxide, dimethylformamide, hexamethylphosphorotriamide, or mixtures thereof).

In some embodiments, the solvent(s) is removed from the extracted component of interest, e.g., prior to further processing of the component of interest.

In some embodiments, the solvent(s) is removed by evaporation (e.g., at ambient temperature (e.g., about 20 to about 23.5° C.) or at elevated temperature (e.g., a temperature higher than ambient temperature, e.g., about 27° C., about 30° C., about 32° C., about 35° C., or about 37° C., or greater).

In some embodiments, the solvent(s) is removed by precipitating the component of interest (e.g., by the addition of water), e.g., and removing the solvent supernatant and replacing it with a solvent of choice.

In some embodiments, optimized salt concentrations can be used to selectively precipitate desired components of interest and retain undesired components in the supernatant and vice versa. For example, such an approach can be used to deplete a complex sample of highly abundant protein species (e.g., serum albumin, immunoglobulins, etc.) and enrich for the low abundance proteins of biological significance.

In some embodiments, the plurality of components provides a liquid phase or the plurality of liquid phases. In some embodiments, the liquid phase is a lipid, organic solvent, aqueous buffer, emulsion, or suspension of solid particles. In some embodiments, the liquid phase is formed from a solid phase upon mechanical processing (e.g., one or more of the liquid phases is a component (e.g., ice) which has a melting temperature higher than the temperature of the extraction process (e.g., lower than 0° C.)). Once a mechanical processing step is performed on the sample (e.g., mixture), a phase transition occurs and the component (e.g., ice) which has a melting temperature higher than the temperature of the extraction process melts, becoming a liquid phase).

In some embodiments, the method is performed under hypotonic salt concentrations.

In some embodiments, the method is performed under hypertonic salt concentrations.

In some embodiments, the method is performed under isotonic salt concentrations.

In some embodiments, the salt concentration is altered to selectively precipitate a component of interest and/or to maintain a contaminant in solution.

In some embodiments, the salt concentration is altered to selectively precipitate a contaminant and/or to maintain a component of interest in solution.

In some embodiments, the sample (e.g., mixture) includes a detergent (e.g., SDS).

In some embodiments, the sample (e.g., mixture) is free or substantially free of detergents.

In some embodiments, the sample (e.g., mixture) includes mineral oil.

In some embodiments, the sample (e.g., mixture) includes a buffer (e.g., phosphate buffer solution (PBS)).

In some embodiments, a protein is extracted from a biological membrane.

In some embodiments, a protein is extracted from a lipid phase.

An example of the methods described herein is as follows. Using the methods described herein, a protein, a nucleic acid, or a lipid can be extracted from adipose tissue, brain, nerves, butter, cream, and so forth. A constituent can be extracted from an emulsion or suspension of solid particles such as a pharmaceutical or cosmetic formulation (ointment, lotion, cream, shampoo, conditioner, nanoparticle drug formulation, etc.). A constituent can be extracted from a pharmaceutical formulation in a tablet, capsule or gelcap form. A constituent can be extracted from a multi-phase composition such as emulsion or suspension of solid particles (e.g., ink, paint, lacquer, lubricant, fuel, ingredients for chemical synthesis, etc.), suspension of liposomes, membrane vesicles, and so forth. Oils, terpenes and/or other lipophilic compounds can be extracted from plant material. Various compounds (e.g. alkaloids, flavonoids, isoflavons, proanthocyanidins, anthocyanins) can be extracted from plants (e.g., medicinal plants). Food flavor constituents (e.g., capsaicin) can be extracted from food preparations. A lipid-soluble vitamin (e.g., a tocopherol, carotenoid, lycopene, etc.) can be extracted from plant oils or animal fat. Topical drug formulation constituents can be extracted from skin and underlying tissues.

In some embodiments, a dye is extracted from paint.

In some embodiments, a component is extracted from soil.

In some embodiments, a component is extracted from suspension of solid particles.

In some embodiments, the plurality of components includes an emulsion.

In some embodiments, the plurality of components includes a lipid or a solution of one or multiple components in lipid or a mixture of lipids.

In some embodiments, the plurality of components further includes a protein, lipoprotein, glycoprotein, glycolipid, steroid, vitamin, drug substance, or drug metabolite. In some embodiments, the plurality of components includes a cell or a single cell organism.

In some embodiments, the method partitions the plurality of components among the plurality of liquid phases, the method includes
  providing a sample (e.g., mixture), wherein the sample (e.g., mixture) comprises the plurality of components and the plurality of liquid phases, wherein the plurality of liquid phases are fractionated;
  performing a first mechanical processing step on the sample (e.g., mixture), wherein the mechanical processing increases the mutual solubility of the plurality of liquid phases, thereby mixing the plurality of liquid phases of poor mutual solubility and resulting in the formation of a metastable mixture; and
  performing a first mechanical processing step on the sample (e.g., mixture), thereby decreasing the solubility of the liquid phases and causing separation of the plurality of liquid phases into fractions and resulting in the partitioning of the components among the plurality of liquid phases.

In some embodiments, the plurality of liquid phases have poor mutual solubility at ambient temperature.

In some embodiments, the disclosure provides a method of extracting a component of interest from a plurality of components. The method includes:
  providing a sample (e.g., mixture) that includes a plurality of components and a plurality of liquid phases, wherein the sample (e.g., mixture);
  performing a second mechanical processing step on the sample (e.g., mixture), wherein the second mechanical processing step is a different type of mechanical processing than the first mechanical processing step and at least two liquid phases in the plurality of liquid phases become partially miscible, resulting in formation of a mixed liquid phase possessing altered properties and leading to a dissolution of at least one component; and
  performing a third mechanical processing step on the sample (e.g., mixture), wherein the third mechanical processing step is a different type of mechanical processing than the first or second mechanical processing step and wherein performing the third mechanical processing step on the sample (e.g., mixture) results in the separation of the component of interest from the plurality of components, thereby extracting the component of interest from the plurality of components.

In some embodiments, the resulting liquid phases containing the plurality of components are separated as fractions.

In some embodiments, a liquid phase(s) includes a solvent.

In some embodiments, the resulting liquid phase (e.g., organic phase) containing the protein(s) of interest can be analyzed directly or the solvent can be removed for further processing of the liquid phase containing the protein(s) of interest.

In some embodiments, the solvent can be removed by evaporation (e.g., at ambient temperature (e.g., about 20 to about 23.5° C.) or at elevated temperature (e.g., a temperature higher than ambient temperature, e.g., about 27° C., about 30° C., about 32° C., about 35° C., or about 37° C., or greater).

In some embodiments, the solvent can be removed by precipitating the protein(s) of interest, removing the solvent supernatant and replacing it with a solvent of choice.

In some embodiments, optimized salt concentrations can be used to selectively precipitate desired proteins and retain undesired proteins in the supernatant and vice versa. For example, such an approach can be used to deplete a complex sample of highly abundant protein species (e.g., serum albumin, immunoglobulins, etc.) and enrich for the low abundance proteins of biological significance.

Other features of the methods described herein include:

In some embodiments, the disclosure provides a protein extraction method where cyclic pressure is used to facilitate sample dissolution. A sample may contain proteins and/or lipids such as triglycerides, phospholipids, glycolipids, sphingolipids, etc., or other hydrophobic compounds, e.g., fatty acids, aliphatic hydrocarbons, etc.

In some embodiments, a sample may contain one or more proteins.

In some embodiments, a sample may contain one or more lipids.

In some embodiments, a sample may contain or be a piece of adipose tissue.

In some embodiments, a sample may contain or be a brain tissue.

In some embodiments, a sample may contain or be an emulsion, suspension or colloid.

In some embodiments, a sample may contain or be milk, a milk product, tree sap, etc.

In some embodiments, a sample may contain or be paint, an industrial lubricant, a cosmetic, e.g., cream or lotion.

In some embodiments, dissolution is facilitated by mechanical processing, e.g., mechanical homogenization, ultrasonic cell disruption, agitation, mixing, impact of glass, ceramic or metal beads, grinding or blending.

In some embodiments, a liquid phase contains or is HFIP, TFE, PFOA, Trichloroethanol, Trifluoroacetic acid or other halogenated alcohol or acid.

In some embodiments, a liquid phase contains or is other organic solvent (e.g., as described herein).

In some embodiments, a liquid phase contains or is water or aqueous buffer (e.g., mixed with an organic solvent).

In some embodiments, a liquid phase contains or is a mixture of several solvents described herein.

In some embodiments, partitioning is done by stationary incubation (e.g., temperature range −20 to +50° C.).

In some embodiments, partitioning is facilitated by centrifugation (e.g., relative centrifugal force: range 1×g (e.g., no spinning) to 40,000×g)).

In some embodiments, partitioning is facilitated by addition of a hydrophobic liquid phase (e.g., oil, lipid, mineral oil, aliphatic hydrocarbon, etc., or a mixture thereof) to the sample to promote phase separation, if sample-derived hydrophobic material is insufficient to form a layer.

In some embodiments, partitioning is done by any combination of the methods described above.

In some embodiments, sample dissolution occurs, but no partitioning is observed (e.g., too little lipid present).

In some embodiments, at least one liquid phase is formed after sample dissolution.

In some embodiments, liquid phases are physically separated by pipetting, decanting, absorption, etc.

In some embodiments, liquid phases are separated using column chromatography (an example of absorption).

In some embodiments, a sample (polar phase) is diluted to induce precipitation following separation of liquid phases.

In some embodiments, liquid phases are not separated, the sample is instead diluted to induce precipitation.

The term "miscible" or "miscibility" refers to the property of liquids to mix in all proportions, forming a homogeneous solution. Water and ethanol, for example, are miscible in all proportions. Substances are said to be "immiscible" or "not miscible" if in any proportion, they do not form a solution.

The term "soluble" or "solubility" refers to the ability of one substance to dissolve in another. Substances are said to be "insoluble" or "not soluble" or "poorly soluble" if one substance is not able to be dissolved in the other substance, e.g., at least about 90% (by weight), about 92%, about 95%, about 96%, about 97%, about 98%, about 99%, or about 100% of the substance is not soluble (not able to be dissolved). Substances are "fully soluble" if one substance is able to be dissolved in the other substance, e.g., at least about 90% (by weight), about 92%, about 95%, about 96%, about 97%, about 98%, about 99%, or about 100% of the substance is soluble. Substances are "partially soluble" if one substance is able to be dissolved to an extent in the other substance, e.g., at least about 10% (by weight), about 15%, about 20%, about 25%, about 30%, about 35%, about 40%, about 45%, about 50%, about 55%, about 60%, about 65%, about 70%, about 75%, about 80%, about 85%, or up to about 90%, of the substance is soluble.

A solid has a definite volume and shape.

A liquid has a definite volume, but is able to change its shape, e.g., by flowing.

Gases have no definite volume or shape.

All herein cited patents, patent applications, and references are hereby incorporated by reference in their entireties. In the case of conflict, the present application controls.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A and 1B are diagrams illustrating pressure cycles.

DETAILED DESCRIPTION

Figure 2:
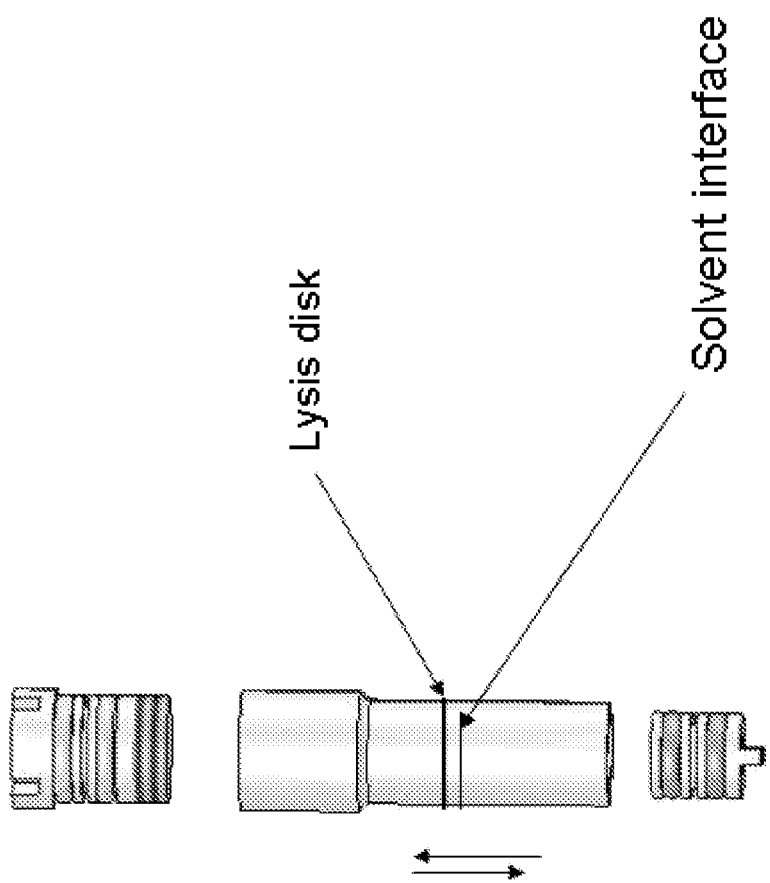
FIG. 2 is a schematic depicting a device that can be used for the partitioning of components and solvents.

Extraction and subsequent analysis of various components of a sample, e.g., a complex biological sample, is important to pharmaceutical development, diagnostics, and biomedical and environmental research.

Many analytical methods use a solution of molecular entities being analyzed, however, many samples (e.g., the majority of biological samples) exist as colloids, gels, highly organized and/or compartmentalized mixtures of various immiscible compounds, such as lipids, proteins, nucleic acids, small molecular entities, and so forth. Such complex systems typically contain molecular entities possessing a wide variety of physiochemical properties, such as solubility or miscibility in a particular solvent, hydrophobicity, electrostatic charge, size, and conformation. Some of the molecular entities (e.g., cytoplasm, vacuoles, organelles) are surrounded by lipid barriers such as biological membranes, while others (e.g., membrane proteins, lipid rafts) are embedded in the lipids.

The diversity of physiochemical properties of molecular entities often results in inadequate recovery of certain classes of molecular entities in a given extraction solvent. For example, aqueous extraction buffers may recover some constituents of the cytoplasm, such as soluble proteins and small molecules, while leaving behind hydrophobic membrane proteins and lipids.

The present disclosure describes methods of extraction, and in some cases dissolution, of molecular entities from sources such as cells and tissues. The extraction is based on the choice of chemical reagents. Factors that can influence the extraction include one or more of: choice of solvent, choice of buffer, choice of multi-phase mixtures (e.g., of immiscible reagents (such as liquids, gases or solids), reaction temperature, and choice of detergent. In some embodiments, the reagents are used in combination with cycles of pressure (e.g., hydrostatic pressure). Factors that can influence the extraction can also include one or more of: maximum pressures, minimum pressures, number of pressure cycles, and length of pressure cycles. In some embodiments, the reagents are used in combination with mechanical processing. Factors that can influence the extraction can also include one or more of: the type of mechanical processing used, the duration of the mechanical processing, the strength of the mechanical processing applied, and so forth.

Features of the methods described herein include:
extractions employing less or no surfactants or detergents;
direct compatibility with downstream analytical applications such as liquid chromatography, electrophoresis and mass spectrometry;
higher recovery yields (and/or better quality yields) of hydrophobic proteins;

more complete extraction of hydrophobic molecules from samples containing high amounts of lipids, e.g., adipose or brain tissue, or a sample enriched in biological membranes;

single-step extraction of more than one class of molecular entities (e.g., proteins, lipids, nucleic acids, and small molecule metabolites; pesticides and drugs of abuse, pharmaceutical preparations; nanoparticle formulations; food constituents, etc.);

convenient format for sample handling and fractionation;

alternative fractionation technique that allows one to extract analytes from the sample that are not extractable by conventional methods;

alternative fractionation technique that allows one to determine if conventional methods fail to extract certain analytes from the sample;

fluorinated alcohols and/or other amphiphylic solvents, or combinations thereof, allow a single extraction reagent to produce a lipid extract and a polar extract as two distinct fractions;

pressure cycling facilitates tissue homogenization and clean separation of fractions; and the methods can facilitate control over micelle formation—and provide procedures to create or modify colloids, nanoparticles, emulsions with desired characteristics.

Pressure

Hydrostatic pressure (e.g., pressure cycling) can be used to alter mutual solubility or miscibility of solvents in mixtures (e.g., azeotropic mixtures, solutions, suspensions, or multi-phase mixtures); to control the arrangement of molecules in micelles, emulsions, gels or colloids; and/or to control the dissolution of one or more components of the multi-phase mixture in another component or solvent. Changes in pressure can lead to changes in mutual solubility of the components and depressurization of the system can cause the mixture to break into multiple phases, thereby separating molecules into separate phases based upon the physiochemical properties.

Hydrostatic pressure can be used to prepare colloids or nanomaterials by dissolving components in one solvent, mixing the first solvent with another solvent, thereby leading to the formation of immiscible multi-phase mixtures when the first solvent is under atmospheric pressure. Pressure can also be used to control the size of micelles in a multi-phase system or emulsion to alter its physical property or stability.

The pressure can be applied as e.g., hydraulic or pneumatic pressure.

A pressure cycle is the summation of exposing a sample to more than one pressure for a period of time at each pressure, e.g., raising the pressure and lowering the pressure, e.g., up from a first pressure to a second pressure and then down from the second pressure to a third pressure. Further, a second pressure cycle can be carried out, e.g., from the third pressure to a fourth pressure to a fifth pressure, and so forth. This process can be repeated. For example, a pressure cycle can consist of exposing a sample (e.g., the mixture being exposed to pressure cycles, e.g., the mixture containing a component of interest) to a first pressure for a first period of time and exposing a sample to a second pressure for a second period of time and then exposing the mixture to a third pressure for a third period of time. However, there is no limit to the number of pressures the sample can be exposed to, and the period of time spent at each pressure does not have to be the same. Examples of pressure cycles are provided in FIGS. 1A and 1B. As illustrated in FIG. 1B, a sample is exposed to a first pressure for a period of time ($t_1$). The sample is then exposed to a second pressure for a period of time ($t_2$). The sample is then exposed to a third pressure for a period of time ($t_3$). The sample can be exposed to various pressures for various periods of time ($t_n$). The summation of these exposures to each pressure for each period of time is a pressure cycle. In some embodiments, the sample is exposed to a pressure that is greater than the first or second pressures for a period of time (illustrated as $t_{n-1}$ in FIG. 1B). Exposure to this pressure can, for example, introduce a reagent(s) into the mixture being exposed to the pressure cycles or a chamber (e.g., the chamber containing the mixture that is being exposed to pressure cycles) by rupturing a secondary container containing such reagent.

The maximum pressure to be used can be between about 100 MPa to about 1,000 MPa, e.g., about 100 MPa to about 900 MPa, about 200 MPa to about 800 MPa, about 300 MPa to about 700 MPa, about 400 MPa to about 600 MPa, about 100 MPa to about 350 MPa, about 250 MPa to about 500 MPa. For example, the maximum pressure can be from about 15 to about 35 kpsi (35 kpsi=235 mPa), or about 80 kpsi (537 MPa), or about 30 kpsi, or about 240 MPa.

The minimum pressure to be used can be between about 133 Pa to about 200 MPa, e.g., about 150 Pa to about 150 MPa, about 200 Pa to about 100 MPa, about 350 Pa to about 75 MPa, about 500 Pa to about 50 MPa, 750 Pa to about 35 MPa, about 1 MPa to about 25 MPa, about 1 kPa to about 1 MPa, about 25 kPa to about 250 kPa, about 50 kPa to about 500 kPa, about 100 kPa to about 300 kPa, about 250 kPa to about 750 kPa, about 1 MPa to about 100 MPa, about 25 MPa to about 200 MPa, about 50 MPa to about 100 MPa, about 100 MPa to about 200 MPa, about 135 Pa to about 500 Pa, about 150 kPa, about 100 MPa. In some embodiments, the minimum pressure used is atmospheric pressure at sea level, e.g., about 100 kPa (e.g., 0.1 MPa) e.g., 101.3 kPa.

In some embodiments, the maximum and minimum pressures chosen are based on providing a minimum or maximum difference in pressure values. For example, the minimum and maximum pressures differ by no more than 200 MPa. As another example, the minimum and maximum pressures differ by no less than 100 kPa.

The number of pressure cycles (e.g., the number of times the pressure is raised and subsequently lowered, e.g., the number of times the pressure is changed from a first value to a second value to a third value (e.g., that is lower than the second value)) used is also a factor that affects the extraction. For example, the number of pressure cycles can range between about 1 cycle to about 1000 cycles, e.g., from about 5 cycles to about 800 cycles, from about 10 cycles to about 500 cycles, from about 20 cycles to about 250 cycles, from about 30 cycles to about 150 cycles, from about 50 cycles to about 100 cycles, from about 100 to about 300 cycles, from about 200 to about 400 cycles, from about 50 to about 150 cycles, from about 5 to about 35 cycles, from about 10 to about 25 cycles. In some embodiments, the pressure cycles from a first pressure to a second pressure (e.g., that is higher than the first pressure) to a third pressure (e.g., that is lower than the second pressure; the third pressure may not be the same as the first pressure), and so on. In these embodiments, all three (or more) pressures are included as being part of the cycle.

The length of the pressure cycles (the total amount of time spent in the cycle, i.e., the amount of time spent at the first pressure plus the amount of time spent at the second pressure, plus the amount of time spent at any additional pressure(s) (e.g., at a third pressure, a fourth pressure, etc.)) is also important. For example, the length of the cycle may be from about 5 seconds to about 60 minutes, e.g., about 10 seconds, about 20 seconds, about 30 seconds, about 45 seconds, about 60 seconds, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 15 minutes, about 20 minutes, about 25 minutes, about 30 minutes, about 35 minutes, about 40 minutes, about 45 minutes, about 50 minutes, about 55 minutes, about 60 minutes. In many embodiments, the length of time at the first and second pressures is the same. For example, in a 20 second cycle, the mixture is at the first pressure for 10 seconds and at the second pressure for 10 seconds.

The length of time spent at a given pressure level (e.g., at the first or second or third pressure) can be, e.g., from about 5 seconds to about 30 minutes, e.g., about 10 seconds, about 20 seconds, about 30 seconds, about 45 seconds, about 60 seconds, about 2 minutes, about 3 minutes, about 4 minutes, about 5 minutes about 6 minutes, about 7 minutes, about 8 minutes, about 9 minutes, about 10 minutes, about 11 minutes, about 12 minutes, about 15 minutes, about 20 minutes, about 25 minutes, about 30 minutes. In many embodiments, the length of time at the first and second pressures is the same. For example, in a 20 second cycle, the mixture is at the first pressure for 10 seconds and at the second pressure for 10 seconds.

The exposure to a particular pressure level may need to be optimized based on the properties of solvents and composition of the plurality of components. Thus, the length of time spent at one pressure may need to be longer than the time spent at the other pressure(s). In some embodiments, the mixture may be at each pressure for a different amount of time. For example, the mixture can be at the first pressure for 10 seconds and at the second pressure for 30 seconds.

Further examples of pressure cycles are as follows:

Start at the atmospheric pressure at sea level (101.3 KPa), followed by 100 MPa held for 5 seconds and 30 seconds held at the atmospheric pressure at sea level (101.3 KPa), 20 cycles;

Start at the atmospheric pressure at sea level (101.3 KPa), followed by 20 seconds at 240 MPa and 20 seconds at the atmospheric pressure at sea level (101.3 KPa), 50 cycles; and Start at 100 MPa, followed by 413 MPa held for 10 seconds followed by 200 Mpa held for 10 seconds followed by 100 MPa held for 10 seconds, the sequence repeated over 10 cycles.

In some embodiments involving three pressures in the cycle, the length of the pressure cycle is the total amount of time spent at the first, second, and third cycles.

Examples of pressure cycling parameters include: five one-minute cycles at 35 kpsi, where pressure is kept at 30 seconds at 241 MPa, followed by 30 seconds at approximately 101.3 KPa (atmospheric pressure); 20 cycles where a pressure of 100 MPa held for 5 seconds and atmospheric pressure (101.3 KPa) held for 30 seconds within each cycle; 30 cycles where pressure is maintained at 500 MPa for 10 seconds, followed by the step at 200 MPa for 20 seconds, which is then followed by 30 seconds at 100 MPa, resulting in a 1 minute for each pressure cycle.

Processing Steps

Processing (such as mechanical processing) can be used, e.g., in combination with the solvents described herein and/or in combination with a change in pressure, to alter solubility or miscibility of sample components and/or solvents in mixtures (e.g., azeotropic mixtures, solutions, suspensions, or multi-phase mixtures); to control the arrangement of molecules in micelles, emulsions, gels or colloids; and/or to control the dissolution of one or more components of the multi-phase mixture in another component or solvent. Following mechanical processing components of the system can separate into multiple phases, thereby partitioning molecules into separate phases based upon the physiochemical properties.

Processing (such as mechanical processing) can be used, e.g., in combination with the solvents described herein and/or in combination with a change in pressure, to prepare a suspension, a slurry, an emulsion, micelles, an additional liquid phase, colloids, or nanomaterials by dissolving components in one solvent, and/or mixing the first solvent with another solvent, thereby leading to the formation of immiscible multi-phase mixtures.

Examples of processing include: temperature, microwave radiation, and mechanical processing.

Examples of mechanical processing include: homogenizing (e.g., physical homogenization, e.g., bead beater, sonication, rotor-stator homogenizer, Dounce homogenizer, Potter-homogenizer), vortexing, sonicating, pipetting, shearing (e.g., syringe shearing), grinding (e.g., mortar and pestle grinding), shaking, mixing, blending, hammering, and so forth. Mechanical processing can include a mass transfer step (e.g., vigorous mixing, mechanical shaking, or hammering).

Processing (such as mechanical processing) can be controlled and/or adjusted. Variables include: the duration of the processing, the number of times the processing step is repeated, the strength of the processing step (e.g., force applied to sample), the temperature at which the processing is performed, and so forth.

One or more types of processing (such as mechanical processing) can be used with a method provided herein. Further, one or more types of processing (such as mechanical processing) can be combined with pressure cycling in a method provided herein.

Temperature

The temperature at which the extraction methods are performed can also influence the process. Temperature can increase the disorder of samples (e.g., biological membranes) and facilitate the extraction of a molecular entity (e.g., component) of interest.

For example, the extraction methods can be performed at between about −40° C. to +100° C., e.g., from about −20° C. to about 70° C., from about 0° C. to about 50° C., from 4° C. to about 37° C., from about 10° C. to about 30° C., from about 15° C. to about 25° C., at about 20° C., at about 23° C., at about 25° C., at about 70° C., or at about −2° C.

The choice of temperature for use in the methods can be influenced by the properties of the solvents and sample components. The temperature can be optimized by altering (increasing or decreasing) the temperature in 1° C. increments. The temperature at which the method is carried out can be regulated, e.g., by a circulating water bath.

The extraction methods can also be carried out such that the temperature and the pressure vary within each cycle, since temperature changes further alter mutual solubility of solvents and sample components, i.e., temperature and pressure can be used synergistically. For example, at the first pressure in the cycle, the sample (mixture) is at a first temperature; at the second pressure of the cycle, the sample (mixture) is at a second temperature. In some embodiments, the first temperature is higher than the second temperature. In other embodiments, the second temperature is higher than the first temperature.

The extraction methods can also be carried out such that the temperature varies with processing (such as mechanical processing), since temperature changes further alter mutual solubility of solvents and sample components, i.e., temperature and mechanical processing can be used synergistically. For example, prior to processing (such as mechanical processing), the sample (mixture) is at a first temperature; during processing (such as mechanical processing), the sample (mixture) is at a second temperature. In some embodiments, the first temperature is higher than the second temperature. In other embodiments, the second temperature is higher than the first temperature.

Liquids

A variety of liquids can be used in the liquid phases of the extractions methods provided herein. For example, solvents, detergents, buffers, chaotropic agents (e.g., chaotropic salts), and mixtures thereof can be used.

Solvents

A variety of solvents can be employed in the extraction methods described herein. For example, the solvent(s) can be aqueous, organic, or lipid. The solvent system can form multi-phase mixtures (e.g., of immiscible reagents), for example, the system can be biphasic or triphasic.

In preferred embodiments, at least two solvent phases (e.g., liquid phases) are used and at least two solvent phases are not miscible at one of the pressures of the pressure cycle (e.g., the solvent phases are not miscible at the first pressure). However, upon pressure cycling, the two solvent phases become at least partially miscible (and in some cases, partially soluble) at the other pressure (e.g., at the second pressure, where the second pressure is greater than the first pressure). Upon return to the first pressure (or transition to a third pressure that is lower than the second pressure), the partial mutual miscibility is lost and the solvent phases separate. In some embodiments, depending on the choice of solvent phases used, the solvent phases can become fully miscible (and in some cases, fully soluble) at the second pressure.

In other preferred embodiments, at least two solvent phases (e.g., liquid phases) are used and at least two solvent phases are not miscible prior to processing (such as mechanical processing) (e.g., the solvent phases are not miscible). However, upon processing (such as mechanical processing), the two solvent phases become at least partially miscible (and in some cases, partially soluble). Upon cessation of (or a decrease in) processing (such as mechanical processing), the partial mutual miscibility is lost and the solvent phases separate. In some embodiments, depending on the choice of solvent phases used, the solvent phases can become fully miscible (and in some cases, fully soluble) upon processing (such as mechanical processing).

Examples of solvents include acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethyl ether, diethylene glycol, diglyme (diethylene glycol dimethyl ether), 1,2-dimethoxy-ethane (glyme, DME), dimethylether, dimethyl-formamide (DMF), dimethyl sulfoxide (DMSO), dioxane, ethanol, ethyl acetate, ethylene glycol, glycerin, heptane, hexamethylphosphoramide (HMPA), hexamethylphosphorous triamide (HMPT), hexane, methanol, methyl t-butyl ether (MTBE), methylene chloride, N-methyl-2-pyrrolidinone (NMP), nitromethane, pentane, petroleum ether (ligroine), 1-propanol, 2-propanol, pyridine, tetrahydrofuran (THF), toluene, triethyl amine, water, heavy water ($D_2O$), o-xylene, m-xylene, p-xylene, and mixtures thereof.

Solvents can also be classified as protic or aprotic. Examples of protic solvents include water, methanol, ethanol, formic acid, hydrogen fluoride, and ammonia. Examples of aprotic solvents include dimethyl sulfoxide, dimethylformamide, hexamethylphosphorotriamide, and mixtures thereof.

Mixtures of any of the solvents described herein can also be used.

Non-limiting examples of solvents useful for practicing the methods of this disclosure include chloroform, tetrachloroethylene, methanol, isopropanol, ethanol, water, aliphatic hydrocarbons (e.g., hexane, heptane), acetonitrile, formic acid, trifluoroacetic acid, glycerol, a lipid (e.g., triglyceride, phospholipid, sphingolipid, glycolipidsoil, e.g., from sample itself, e.g., from a biological membrane (e.g., lipid membrane; lipid bilayer)), or aqueous solution (e.g., a liquid component(s) that originates from the sample itself, e.g., from a biological membrane or cytoplasm), a fluorocarbon, other halocarbon, dimethyl sulfoxide (DMSO), fluorinated alcohols (e.g., amphiphilic fluorinated alcohols) (e.g., 1,1,1,3,3,3-hexafluoro-2-propanol (HFIP), 2,2,2-trifluoroethanol (TFE), 2-fluoroethanol, 2,2,3,3-tetrafluoropropan-1-ol, 1.3-difluoropropan-2-ol, perfluorooctanol), other alcohols, and mixtures thereof. In some embodiments, a sample (e.g., the source of components) provides (e.g., functions as) a solvent. In some cases, this solvent from the sample constitutes one of the liquid phases of the extraction system. For example, in the extraction of a membrane protein, under appropriate conditions, the lipid bilayer acts as a solvent and as a liquid phase in the extraction method (e.g., the membrane protein is dissolved in the lipid bilayer).

The concentrations of the solvent can be optimized. Examples of concentrations include: about 0.2M HFIP; about 0.05M HFIP; about 0.38M to about 0.57M HFIP; about 60% HFIP; about 75% HFIP; about 95% HFIP; about 100% HFIP; about 1% to about 5% formic acid. The solvents can be made up in various other solvents (e.g., acetonitrile) or buffers (e.g., phosphate buffered solution (PBS)). The solvents can be used by themselves to constitute a phase in the methods described herein. Alternatively, a solvent (e.g., a solvent listed herein) can be a solvent that, along with another component (e.g., a liquid, e.g., another solvent) make up one solvent phase. For example, 50% acetonitrile with 0.1% formic acid can make up on solvent phase, as illustrated in the examples herein.

A single solvent phase can include a combination of solvents. For example, a solvent phase can be chloroform: methanol:water in a 2:5:2 or 4:4:1 (w:w:w) ratio; or methanol:chloroform in a 1:1 (w:w) ratio. As another example, 50% acetonitrile with 0.1% formic acid can be used as a solvent phase.

The solvents can include an azeotrope, or an azeotrope can form when solvent phases are exposed to increased (e.g., second) pressure. While azeotropic properties of solvent mixtures have been predominantly studied in applications of distillation, since the boiling temperature of a resulting azeotrope is different from the boiling points of its ingredient solvents, azeotropic mixtures act as different solvents by exhibiting altered solubility and ability to dissolve other compounds. Hydrostatic pressure alters the properties of azeotropic solvent mixtures as it alters properties of individual solvents. Examples of azeotropes that can be present in a solvent phase or that can form upon exposure to the second pressure include 95.5% ethanol and 4.5% water (w:w); 20.2% hydrogen chloride and 79.8% water (w:w); 1.2% water and 98.8% diethyl ether (w:w); 20% acetone and 80% chloroform (w:w); 30% acetone, 47% chloroform, and 23% methanol (w:w:w).

In some embodiments, one or more solvents are added to a sample (e.g., source of components for extraction) and this leads to the formation of two or more liquid phases. For example, the addition of a solvent e.g., an amphiphile such as HFIP, to a sample that contains one or more hydrophilic and/or polar components and one or more lipids results in the formation of stable mixtures with the one or more hydrophilic and/or polar components and the one or more lipids (e.g., upon exposure to an increased pressure level or upon processing (such as mechanical processing)). When pressure is decreased or upon cessation of (or a decrease in) processing (such as mechanical processing), the one or more hydrophilic and/or polar phases (e.g., HFIP) and one or more lipids separate into two or more liquid phases, e.g., thereby leading to the separation of components into the hydrophilic and/or polar or lipid phases, e.g., leading to the separation of a component of interest. In some preferred embodiments, one solvent is added to a sample (e.g., source of components for extraction) and this leads to the formation of two or more liquid phases, e.g., the sample provides a solvent(s) (e.g., liquid phase). For example, the addition of a solvent e.g., an amphiphile such as HFIP, to a sample that contains water and lipids results in the formation of stable mixtures with water and the lipids (e.g., upon exposure to an increased pressure level or upon processing (such as mechanical processing)). When pressure is decreased or upon cessation of (or a decrease in) processing (such as mechanical processing), the water (e.g., and HFIP) and lipids separate into two or more liquid phases, e.g., thereby leading to the separation of components into the water and lipid phases, e.g., leading to the separation of a component of interest.

In some embodiments, an organic solvent, (e.g., a volatile organic solvent) (e.g., HFIP) may need to be removed. For example, the removal of a volatile organic solvent can be accomplished by evaporation. In some embodiments, the removal of the volatile organic solvent can be accomplished by precipitation of the component(s) of interest. Subsequently, remaining solvent can be separated from the resulting pellet. Precipitation can be accomplished from a solvent, e.g., HFIP, by the addition of the appropriate component, e.g., an aqueous solution. Precipitation efficiency can be modified by sample concentration, temperature, pH, time, pressure and the addition of other solutes, e.g., salts, chaotropic agents, detergents or other components.

Buffers

A variety of buffers can be used with the extraction methods described herein. For example, PBS can be used in a solvent phase of the methods. A wide variety of buffers can be used to maintain a desired pH of an extraction solvent and to maintain the solubility of desired components in a particular solvent and compatibility with a subsequent analytical method. Examples of such buffers include HEPES, TRIS, MES, ammonium bicarbonate, ammonium acetate, formic acid, trifluoroacetic acid, acetic acid, etc.

Various concentrations of salts can be used to control osmotic pressure during selective extraction of cellular material. For example, 0.9% sodium chloride can be used in the extraction of various components from mammalian cells. Osmotic pressure can act synergistically with processing (such as mechanical processing), or with hydrostatic pressure in pressure cycling applications. For example, hypotonic concentrations of salts in the extraction solution can result in cell swelling and can act synergistically with processing (such as mechanical processing), or with the pressure cycling treatment to disrupt cellular plasma membranes. Conversely, hypertonic salt concentrations can be used to protect cells from disruption at certain pressure cycling (or processing (such as mechanical processing)) conditions, if such a result is desired. For example, for mammalian cells, NaCl concentrations below about 0.9% are hypotonic, and concentrations above about 0.9% are hypertonic.

Detergents and Chaotropic Agents

A detergent or a chaotropic agent (e.g., chaotropic salt) can be added to a solvent phase to aid in the extraction of a molecular entity (e.g., component) of interest. In some embodiments, the amount of detergent or chaotropic agent used can be less than the amount used for known partitioning techniques, such as techniques that do not employ the solvents described herein or that are based on mechanical shaking (e.g., in the absence of the solvents described herein). In some embodiments, when a detergent is used in the methods described herein, no foaming is formed during the extraction.

Examples of detergents that can be used include anionic detergents (e.g., SDS, Cholate, Deoxycholate); cationic detergents (e.g., C16TAB); amphoteric detergents (e.g., LysoPC, CHAPS, Zwittergent 3-14); and non-ionic detergents (e.g., Octylglucoside, Digitonin, C12E8, Lubrol, Triton X-100, Nonidet P-40, Tween 80). Several amphiphylic organic solvents, such as fluorinated alcohols (HFIP, TFE, perfluorooctanol, etc.) are frequently regarded as possessing detergent functionality. Such solvents can be used alone or in combination, as an additive to other solvents and buffer systems, e.g., solvent and buffer systems described herein.

The concentration of detergent used can be, for example, from about 0.001% to about 10%, e.g., about 0.1% to about 2%, e.g., about 0.5% to about 4%, e.g., about 1% to about 2%.

In some embodiments, the liquid phases (e.g., combined liquid phases) are free or substantially free of detergent.

A chaotropic agent can also be used. Examples of such agents include urea, guanidinium chloride, guanidinium isothiocyanate, and guanidine hydrochloride. The concentration used can be about 0.1 M to about 8M. Examples of chaotropic agents include those described, e.g., in U.S. Pat. No. 7,064,192 and U.S. Published App. Nos. 2006-0188970; 2004-0038333; 2003-0083475; and 2002-0137157.

Other Components in the Liquids

The liquid phases described herein can optionally contain additional reagents. For example, an enzyme inhibitor, e.g., one or more of protease inhibitors (e.g., inhibitors of serine, cysteine, and aspartic proteases and aminopeptidases) (e.g., 4-(2-aminoethyl)benzenesulfonyl fluoride (AEBSF), pepstatinA, E-64, bestatin, leupeptin, and aprotinin), DNAse inhibitors (e.g., aurintricarboxylic acid), RNAse inhibitors (e.g., diethylpyrocarbonate (DEPC), Cesium Trifluoroacetate (CsTFA), recombinant placenta RNAse inhibitor, SUPERASE.IN™, ANTI-RNase or RNASECURE™ (Ambion), SCRIPTGUARD™ (Epicentre Biotechnologies), DEPC), metal chelating agents (e.g., DTPA, EDTA, EGTA, NTA, desferal) and so forth can be added to the liquid phases, e.g., to stabilize a component of interest, e.g., a component being extracted.

As another example, mineral oil can be included in the liquid phases. The addition of mineral oil to the sample can improve band sharpness and intensity. For example, as described in the examples, increasing the amount of mineral oil in a sample can be beneficial, e.g., by improving phase separation to allow for efficient partitioning of endogenous lipids in a sample into the oil layer during centrifugation.

Salt

High concentrations of salt can affect the extent of precipitation of certain proteins. For example, high salt concentrations can interfere with or promote protein precipitation. Typically, endogenous sample-derived salts are insufficient to cause any 30 significant effects upon precipitation. In many instances, exogenous salts can be added to improve total protein precipitation. In addition, optimized salt concentrations can be used to selectively precipitate desired proteins and retain undesired proteins in the supernatant and vice versa. For example, such an approach can be used to deplete a complex sample of highly abundant protein species (e.g., serum albumin, immunoglobulins, etc.) and enrich for the low abundance proteins of biological significance.

A high salt concentration refers to a salt concentration of more than about 1% by weight, based on the total weight of the solution. For example, the salt concentration is at least about 5%; or at least about 10%, by weight, based on the total weight of the solution.

Examples of high salt solutions include: Sodium chloride-saturated solution (35.9 g/100 mL at 25° C.); Ammonium sulfate-saturated solution in water (70.6 g/100 mL at 0° C. or 103.8 g/100 mL at 100° C.); 4M Guanidinium isothiocyanate.

A low salt concentration refers to a salt concentration of less than about 1% by weight, based on the total weight of the solution.

Secondary Containers

In some embodiments of the extraction methods described herein, a secondary container (e.g., capsule, ampule) can be present in the mixture that is being exposed to the extraction methods that are described herein (e.g., methods that include pressure cycles and/or processing (such as mechanical processing)). The contents of the secondary container can include a reagent or multiple reagents which will be introduced to the main container during application of a certain level of pressure or processing (such as mechanical processing) sufficient to cause the secondary container to release its contents (e.g., rupture). In some embodiments, the secondary container can be made out of frozen ingredient (e.g., water). For example, in such embodiments, pressure or processing (such as mechanical processing) melts the secondary container, e.g., and causes it to release its contents. The frozen secondary container can be either inert and used to contain an active ingredient, or the frozen secondary container itself can be the active ingredient (e.g., and the pressure can melt the container that is the active ingredient and thereby cause the container to release its contents).

The reagent(s) introduced during the application of pressure or processing (such as mechanical processing) can either serve as a secondary (or tertiary, etc.) liquid phase to facilitate partitioning of sample components. Alternatively, this reagent can serve as an additive to existing liquid phase(s). The reagents can be used in the extraction methods to e.g., increase the partitioning of a component(s) of interest, increase the solubility of a component of interest, increase the partitioning of a contaminant (e.g., component that is not of interest, e.g., into a phase that does not contain the component of interest), alter the properties of extraction solvent, such as pH, osmotic pressure, etc. Examples of such reagents include organic solvents, amphyphilic solvents; solutions of chaotropic salts or detergents, detergent solution (sodium dodecyl sulfate, [(3-Cholamidopropyl)dimethylammonio]-1-propanesulfonate, (CHAPS), Tween-80), an organic solvent (e.g., hexane, pentane, methanol, ethanol, acetonitrile, methyl-tert-butyl ether (MTBE), n-propyl alcohol, isopropyl alcohol, isopentane, octane, decane, cyclohexane, xylene, benzene, tolyene, etc. or mixtures of thereof, amphiphilic reagent (e.g., HFIP, TFE), salts such as sodium chloride, lithium acetate, ammonium bicarbonate, ammonium acetate, etc; acids or bases such as trifluoroacetic acid, formic acid, acetic acid, ammonium hydroxide, sodium hydroxide, lithium hydroxide, etc.

One or more such reagents can be introduced, e.g., from the same or different secondary containers, e.g., upon pressure cycling to a certain pressure level. For example, the secondary container can be designed to release its contents (e.g., rupture, leak, dissolve, or melt) at or above a certain pressure level. In some embodiments, more than one secondary container can be used. For example, one secondary container can be designed to release its contents at one pressure, while a second secondary container can be designed to release its contents at a second pressure, and so forth. In this way, different reagents (or the same reagent in a separate dose) can be introduced into the mixture at controlled times (e.g., after a certain number of pressure cycles). The secondary containers are not limited in their shape or design. As used herein, the term "secondary container" refers to a form (e.g., sealed form) whose contents include a reagent and that prevents the introduction of the reagent into the mixture or liquid phase contained in the secondary container until the pressure or the processing (such as mechanical processing) is raised to a level that causes the secondary container to release its contents. The material from which the secondary container is prepared is not limited. For example, the secondary container can be made of gelatinous material, cellulosic polymers, glass, polymer (SAN, Polycarbonate, polystyrene, polypropylene, other polymer, etc). The pressure or processing (such as mechanical processing) at which the secondary container will be disrupted will be defined by the rigidity of the secondary container material and the amount of sample and other compressible material (e.g. gas, air, nitrogen, carbon dioxide, oxygen, inert gas: helium, argon, neon, etc.) inside the secondary container, and/or by the composition of the container. For example, the secondary container will release its contents (e.g., rupture, leak, or melt) at the pressure levels at which its resistance to compression will be lower then the compressibility of the secondary container contents. The secondary container may also be made, e.g., out of the amorphous or crystalline compound, which melting point is above the sample processing temperature at atmospheric pressure. Application of high pressure will melt the secondary container material. Alternatively, the entire secondary container may be prepared out of the ingredient to be added to the mixture of liquid reagents, e.g., solid ice, solid lipid, paraffin, etc. Such material will become liquid under pressure and can participate in the partitioning of the sample components. It may or may not solidify again upon depressurization of the mixture. If this component does solidify and if it will contain several constituents of the initial mixture, which partitioned into it under pressure, the components can be fractionated out of the mixture by simple removal of the solidified material out of the mixture.

Additional Steps

The methods of extraction described herein can be performed alone or in combination with one or more additional steps/methods to isolate a component of interest. The additional step(s) can be performed before or after an extraction method described herein. For example, centrifugation (e.g., gradient centrifugation or ultracentrifugation) (e.g., centrifugation in the same vessel in which an extraction method described herein is performed), precipitation (e.g., precipitation of one or more sample components), immunoprecipitation (e.g., to remove a contaminant), permeablization (e.g., of a cell, e.g., using a detergent), using hypotonic buffer conditions to disrupt the plasma membrane or other membranes surrounding organelles, enrichment for a particular tissue, cell or organism type, membrane fraction, etc.; fractionation of sample constituents according to their localization in the cell or tissue or according to their physiochemical properties (e.g., electrostatic charge, hydrophobicity, solubility in a particular solvent, molecular conformation or binding affinity, etc.) can be performed along with an extraction method provided herein to improve the isolation or purification of a component of interest.

Sources of Components for Extraction

The extraction methods described herein can be used to extract a component of interest from a sample that contains at least two components if the component of interest has a physiochemical property (e.g., electrostatic charge or solubility in a solvent or solvent system) that differs from that of the other component(s) in the sample.

Examples of sources from which a component can be extracted include biological and synthetic (e.g., man made) sources. Examples of sources of biological origin include mammalian (e.g., human or domesticated animal), fungal, bacterial, viral, and plant sources. Examples of such sources include a cell, an organelle (e.g., mitochondrion, nucleus, Golgi apparatus, chloroplast, endoplasmic reticulum, vacuole, acrosome, centriole, cilium, glyoxysome, hydrogenosome, lysosome, melanosome, mitosome, myofibril, nucleolus, parenthesome, peroxisome, ribosome, microsome, vesicle), a membrane (e.g., a lipid membrane, e.g., a lipid bilayer), a biological sample (tissue sample (adipose tissue, liver, kidney, skin, pancreas, stomach, intestine, colon, breast, ovary, uterine, prostate, bone, tendon, cartilage, hair, nail, tooth, heart, brain, lung, skin, nerves, biopsy, etc.), blood, urine, milk, semen, saliva, mucus, other bodily fluids and solids), collection of cells (e.g., blood, semen, mucus, saliva, tissue biopsy), an ancient sample (e.g., fossil (e.g., fossil animal, fossil wood, fossil bone, fossil tooth, fossil dung, etc.)). Examples of other sources include butter, cream, a pharmaceutical or cosmetic formulation (ointment, lotion, cream, shampoo, conditioner, nanoparticle drug formulation, etc.), a pharmaceutical formulation in a tablet, capsule or gelcap form, a multi-phase composition such as emulsion or suspension of solid particles (ink, paint (e.g., latex paint), lacquer, lubricant, fuel, ingredients for chemical synthesis, etc.), suspension of liposomes, membrane vesicles, liquid propellants, fuels, elastomers, polymers, ink formulations; emulsions of oil in water and other solvents (such as industrial lubricants), soil (e.g., suspensions of soil samples), minerals, and so forth.

Extracted Components

Examples of components (e.g., molecular entities) that can be extracted by the methods described herein include a protein (e.g., membrane bound protein, transmembrane protein, type I or type II membrane protein, receptor, enzyme, a lipoprotein, a glycoprotein), a polysaccharide (e.g., heparin or heparin-derived polysaccharide, starch, inulin, etc.), a proteoglycan (e.g., collagen, chitin, murein, etc.), a polyphenol (e.g., a tannin, a phenylpropanoid (e.g., a lignin, a flavonoid), a vitamin, a toxin, a pollutant, a lipid (e.g., phospholipids (e.g., phosphatidylcholine (PtdCho), phosphatidylethanolamine (PtdEtn), phosphatidylinositol (PtdIns), phosphatidylserine (PtdSer)), glycolipids, steroids (e.g., estrogen, progesterone, androgen, testosterone, ecdysteroids such as ecdysterone, corticosteroids such as glucocorticoids and mineralocorticoids, anabolic steroids, cholesterol, phytosterols, brassinosteroids, ergosterols), a membrane (cell membrane, organelle membrane, lipid bilayer), a nucleic acid (DNA (nuclear DNA, mitochondrial DNA), RNA (mRNA, tRNA, rRNA, mtRNA, microRNA)), a virus (e.g., HIV, HPV, hepatitis A, B, C, D, E, F, or G, cytomegalovirus, Epstein-Barr virus, yellow fever, and so forth), a bacterium (e.g., Gram positive or Gram negative bacteria, mutualist bacteria, pathogenic bacteria), a component present in a bacterial cell or in a cell of other microorganism or other cell type, (e.g., a protein recombinantly produced by the bacterium, yeast or a mammalian cell), recombinant proteins contained within the inclusion bodies, bacterial DNA or RNA, an antigen (e.g., from a bacterium, fungal or mammalian cell or from a virus), a virus (e.g., for vaccine production), a pharmaceutical agent such as a small molecule, a metabolite (e.g., a small molecule metabolite), a pesticide (e.g., bactericide, fungicide, herbicide, insecticide (e.g., ovicide, larvicide or adulticide), miticide, molluscicide, nematicide, rodenticide, virucide), a drug (e.g., a pharmaceutical drug), a drug metabolite, a dye, a food constituent, a nanoparticle formulation, a lipid raft, an amyloid plaque, microtubule, cytosol, oils, terpenes and other lipophilic compounds (e.g., from plant material), various compounds (e.g. alkaloids, flavonoids, isoflavons, proanthocyanidins, anthocyanins) from plants (e.g., medicinal plants), food flavor constituents (e.g., capsaicin) (e.g., from food preparations), lipid-soluble vitamins (e.g., tocopherols, carotenoids, lycopene, etc.) (e.g., from plant oils or animal fat), topical drug formulation constituents (e.g., from skin and underlying tissues), a particular cell type, polymer, elastomer, lubricant, pigment, plasticizer, and so forth. For example, extraction of membrane proteins from lipid-rich adipose tissue or extraction of enzymes such as cytochromes P450 from liver microsomal fraction is greatly simplified and higher yields of desired proteins are obtained.

Examples of cell types include blastomere, egg, embryonic stem cell, epithelial cell, erythrocyte, fibroblast, hepatocyte, leukocyte, myoblast, myotube, neuron, oocyte, osteoblast, osteoclast, sperm, T-cell, zygote (animal or plant), aleurone, collenchyma, endodermis, endosperm, epidermis, mesophylll, meristematic cells, palisade, parenchyma, phloem sieve tube, pollen generative, pollen vegetative, sclerenchyma, tracheids, xylem vessel. Also included are various types of keratinizing epithelial cells, wet stratified barrier epithelial cells, exocrine secretory epithelial cells, hormone secreting cells, gut, exocrine glands and urogenital tract cell, metabolism and storage cells, barrier function cells (lung, gut, exocrine glands and urogenital tract), epithelial cells lining closed internal body cavities, ciliated cells with propulsive function, extracellular matrix secretion cells, contractile cells, blood and immune system cells, sensory transducer cells, autonomic neuron cells, sense organ and peripheral neuron supporting cells, central nervous system neurons and glial cells, lens cells, pigment cells, germ cells, nurse cells.

Analysis of Extracted Components

The extracted component can be analyzed by various methods known in the art. For example, a component of interest (e.g., a phase containing a component of interest) that is purified using the methods described herein can be compatible with downstream processes (e.g., analytical methods) (e.g., compatible with processes that are not compatible with detergents), and/or can be directly used in such processes.

For example, two-dimensional gel electrophoresis; one-dimensional gel electrophoresis, Western blotting, ELISA, protein or peptide mass fingerprinting (e.g., using MALDI-TOF/TOF), multidimensional electrophoresis (e.g., solution phase isoelectric focusing followed by two-dimensional gel electrophoresis of concentrated pI fractions), mass spectrometry (MALDI-MS, LC-MS/MS, MALDI-TOF MS, or LC-ESI-MS/MS), PCR, RT-PCR, and microarrays, thinlayer chromatography, liquid chromatography (e.g., HPLC), gas chromatography, GC/MS, electron microscopy, fluorescent microscopy, and surface analysis methods. In certain embodiments, isolated molecules or complexes thereof may be used in functional assays, e.g., enzymatic activity assays, in-vitro metabolism assays, etc., or subjected to subsequent fractionation or extraction steps.

The phase(s) containing a component(s) of interest obtained from the extraction methods may not require further purification and may be directly compatible with certain methods of analysis, e.g., HPLC and/or LC/MS, GC and/or GC/MS (e.g., due to the absence of detergents, volatility of the solvents and ability to inject the resulting extract directly onto the HPLC column without prior solvent removal). Direct application of sample can minimize the potential loss of components of interest due to degradation or sample manipulation.

Devices

Figure 3:
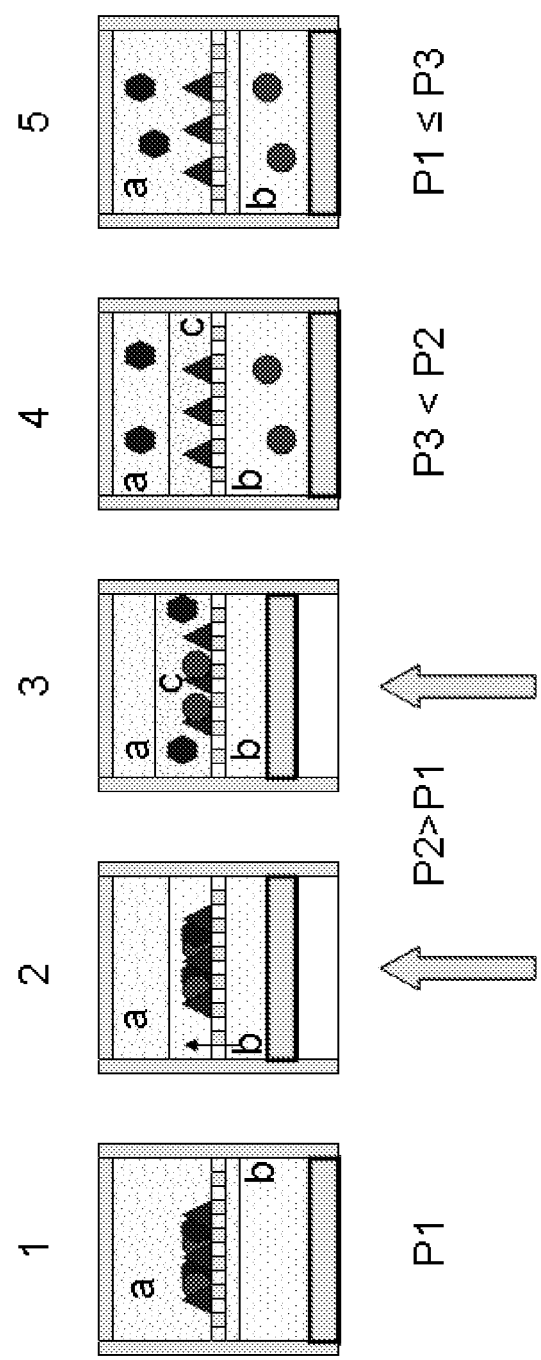
FIG. 3 is a schematic demonstrating liquid-liquid partitioning mediated by pressure cycling.

The extraction methods described herein can be performed in a number of devices, but are not limited to the utilization of a particular device. For example, a device that allows for or facilitates liquid-liquid partitioning of samples (mixtures) can be employed. FIG. 2 provides an example of a single use sample container for dissolution and partitioning of sample components using solvents. Two compartments separated by a perforated disk (lysis disk). This disk can be positioned close to the expected location of the liquid phase boundary. The disk creates turbulent flow when the solvent boundary crosses it, leading to improved mixing of the solvents with the sample material and of multiple solvents with each other. This facilitates mixing of two liquids during pressure cycling. Mass transfer due to pressurization during cycling causes the liquid interface to cross through the disk. Hydrostatic pressure alters mutual solubility of solvents in one another. When solvents are mixed under alternating hydrostatic pressure (e.g., pressure cycling), better dissolution of sample particulate material can be achieved. As illustrated in FIG. 3, the liquid-liquid partitioning mediated by pressure cycling can occur as follows:

1. Immiscible solvents a and b are placed in the sample container with the solid sample containing a plurality of components.

2. Hydrostatic pressure P2 causes compression of the liquid and the solid sample. As the solvent boundary crosses the perforated disk, rapid mixing of the solvents occurs.

3. Incubation under hydrostatic pressure alters the mutual solubility of the solvents leading to a formation of a third metastable solvent c possessing combined properties of solvents a and b. Sample dissolution can occur at this stage.

4. Depressurization of the system to a lower pressure P3 causes expansion of the mixture and separation of solvents a and b and the partitioning of the solutes between solvents a and b according to their partitioning coefficients logP or distribution coefficients logD (for partially dissociated solutes).

5. The system returns back to its original equilibrium at pressure P1. At this stage, the cycle may be repeated to continue the dissolution and partitioning process.

In this example, the perforated disk (lysis disk) is in a certain position. Improvements to current devices that can be made to make the devices more amenable to practicing the methods described herein include: a variable position of the perforated disk; the use of multiple disks; a secondary container—to be inserted into a sample tube (e.g., into the top or bottom compartment)—containing a reagent (e.g., as described herein) to be introduced under pressure as the pressure reaches the level at which the secondary container releases its contents (e.g., ruptures).

EXAMPLES

Example 1

Extraction of Lipids, Proteins and Small Molecules from Plant Tissue

Molecular entities were extracted from plant tissue. The plant tissue was placed in a solvent system containing two solvents. Solvent A was 50% aqueous acetonitrile and 0.1% formic acid; solvent B was chloroform. The two solvents were present as two separate phases. The mixture was sealed in a flexible container. The mixture was treated with 20 cycles at 10 seconds each of pressure cycling. The pressure cycled from atmospheric pressure (101.3 KPa at sea level) to 240 MPa. Upon completion of the cycling, the solvents were partitioned into two separate phases and the molecular entities from the plant tissue were partitioned between the two solvents. Most hydrophilic constituents remained in the top solvent fraction, which consists of predominantly water, formic acid, and less than 50% w/w of acetonitrile. The bottom fraction, which consists predominantly of chloroform and the remaining acetonitrile, contained hydrophobic molecular entities. Both fractions can be subjected to the analysis methods suitable for detection and quantification of respective compounds.

Example 2

Extraction of Lipids and Proteins from Adipose Tissue

Extraction of lipids and proteins from adipose tissue was conducted using a 100 mg tissue sample in pure 1,1,1,3,3, 3-hexafluoro-2-propanol (HFIP). HFIP is an amphiphilic solvent which forms stable uniform mixtures with water and with the lipids which are present in the sample. After sample extraction by pressure cycling, the resulting solutions become immiscible and separate into individual phases upon return to atmospheric pressure. While high pressure maintains partial miscibility of the resulting phases to enhance the partitioning of sample components between them, a decrease in pressure acts as an important factor to promote phase separation. The lipid fraction is subsequently removed (e.g., with the pipette), the HFIP/water fraction is then directly analyzed by HPLC or evaporated to concentrate proteins and nucleic acids. Alternatively, proteins are precipitated out of organic solvent by dilution with excess of water, an aqueous buffer or an aqueous solution of salt and/or other reagent. The protein fraction is reconstituted in a conventional reagent for HPLC or in buffer (detergent-based, e.g., 9M urea/4% CHAPS; or e.g., 2% SDS) to provide compatibility with the gel separation method of choice (e.g., one- or two-dimensional gel electrophoresis).

Example 3

Comparison of Techniques for Protein Extraction from Adipose Tissue

The device shown in FIG. 2 was used for the extraction of proteins from adipose tissue by pressure cycling. The following three extraction reagents were compared:

1. Tris Buffered Saline (TBS), no detergent
2. 9M Urea+4% CHAPS
3. HFIP, an amphiphilic fluorinated alcohol Samples processed in TBS show minimal disruption of adipose tissue and protein extraction remains minimal.

Since high (up to 70% by weight) lipid content sequesters detergents into micelles, the sample processed in Urea/CHAPS is not well dissolved and contains hydrophobic protein which is still associated with the lipid mass. Sample extracted in HFIP does not contain visible residual fat tissue (which appears as a white greasy residue). Instead, in condition 3, the fat and solvent separate into hydrophilic (bottom) and hydrophobic (top) phases. Amphiphilic solvents are capable of dissolving the polar and apolar components equally well while pressure cycling facilitates the extraction process. Resulting extracts separate into two or more phases upon depressurization.

Example 4

Extraction of Lipids, Proteins and Small Molecules from Porcine Adipose Tissue

A comparison of pressure cycling-mediated extraction using several solvents was performed. The solvents compared were: HFIP+0.1% TFA, Tris Buffer+0.9% NaCl and 2% aqueous SDS. 100 mg of tissue in 1.4 ml of each solvent was used. Each sample was subjected to the same pressure cycling conditions: 30 cycles of 240 MPa for 20 seconds and atmospheric pressure for 20 seconds during each cycle. After a first extraction with the three solvents, the resulting hydrophilic phase was analyzed by SDS-PAGE and Coomassie blue staining. Each sample was run in duplicate. Approximately twice as much protein was extracted by the HFIP+0.1% TFA solvent, compared to the 2% aqueous SDS (data not shown). Tris Buffer+0.9% NaCl extracted the least amount of protein.

A second extraction was performed on the residual lipid debris with the same respective solvents. The resulting extracts were analyzed by SDS-PAGE and Coomassie blue staining. The least residual protein was recovered from the sample extracted with the HFIP+0.1% TFA solvent, confirming that a greater amount of protein was extracted in the first extraction under this condition than with the other solvents tested (data not shown).

Example 5

Extraction of Protein from Adipose Tissue: A Comparison of HFIP vs. Detergent

Experiments were performed to compare the effectiveness of HFIP and a 9M urea/4% CHAPS reagent to extract protein from murine adipose tissue with pressure cycling: 30 cycles of 240 MPa for 20 seconds and atmospheric pressure for 20 seconds during each cycle. Two to three times as much protein was extracted with HFIP than with the urea/CHAPS reagent. The results are shown in Table 1.

TABLE 1

Protein yields based on extraction solvent

| | | AVG mg/mL | STDEV |
|---|---|---|---|
| HFIP | Group 1 | 4.48 | 0.36 |
| | Group 2 | 5.87 | 0.54 |
| 9 M urea 4% CHAPS | Group 1 | 2.22 | 0.23 |
| | Group 2 | 2.37 | 0.16 |

Example 6

Rat Brain Protein Extraction—Binary and Ternary Solvent Combinations

Experiments were performed to extract protein from rat brain. The brain tissue does not contain enough endogenous lipid to cause phase separation. Secondary hydrophobic solvent was added to "compensate" for the lack of endogenous lipid and promote phase separation.

All samples were processed with pressure cycling –30 cycles of 20 seconds up, 20 seconds down, 35,000 psi as the high pressure and atmospheric pressure as the low pressure. 50 mg of tissue were used per experimental condition. 5 µl of protease inhibitors were included. Reagents were added to a final volume of 1.4 ml.

The conditions tested were: HFIP; Hexane; Mineral oil; HFIP/hexane 1:2; and HFIP/hexane 1:1.

No phase separation was observed in samples extracted with HFIP alone. Phase separation was observed when HFIP:Hexane, HFIP/mineral oil and HFIP/hexane/mineral oil were used.

Addition of a more volatile reagent (hexane) dramatically speeds up solvent removal by evaporation.

These experiments provide a comparison of extraction with detergents versus extraction with solvents. A reason that SDS fails to pull out all the protein is likely predominantly stoichiometric—there is not enough SDS to dissolve all of the fat—so lengthy mechanical homogenization is typically performed to recover all of the protein molecules buried inside the fat globules. This process usually creates a lot of foam, froth and emulsions, where protein loss is inevitable. Reagents that rely on detergent to dissolve the fat will leave the bulk of fat intact. Conversely, pressure cycling in combination with a solvent such as HFIP, leads to complete dissolution of adipose tissue without the formation of foam or froth.

Example 7

Proteomic Analysis of Adipose Tissue Using Detergent-Free Protein Extraction by Pressure Cycling and High Resolution Tandem Mass Spectrometry Proteomic analysis of adipose tissue is highly valuable for studies of type 2 diabetes, obesity, cancer and many other human disorders. However, conventional protein solubilization methods applied to tissues with high lipid content tend to produce highly variable results, especially with respect to important hydrophobic proteins from mitochondria, ER, plasma membrane and fat droplets. Abundant sample-derived lipids tend to sequester detergents into micelles, thus interfering with protein extraction.

These experiments investigated the use of alternating hydrostatic pressure (Pressure Cycling Technology, or PCT) and a variety of organic solvents for detergent-free disruption of cells, micelles and membrane fragments and increased efficiency of protein recovery from mouse adipose tissue samples as compared to the conventional homogenization and dissolution techniques. Resulting protein extracts were analyzed by SDS-PAGE, 2D-electrophoresis, nano-flow HPLC and high resolution high mass accuracy tandem mass spectrometry.

A novel pressure cycling-assisted liquid-liquid extraction and fractionation method has been developed to achieve nearly complete tissue dissolution and fractionation of lipids and proteins into distinct liquid phases. In addition to the overall higher protein recovery by the novel pressure cycling method, several novel protein species were identified in the pressure cycling extracts of adipose tissue. It has also been demonstrated that many proteins are underrepresented in the extracts obtained using conventional methods. Analysis of several genetically distinct model mouse lines has revealed several trends in protein expression which may be linked to the disease progression or serve as potential drug targets. Lipid fractions resulting from the fractionation have been obtained and collected for future lipid profiling studies.

Sample Preparation by Pressure Cycling Technology (PCT)

The goal of this study was to develop a reliable and reproducible protein extraction method from adipose tissue to enable future proteomic investigations of murine disease model. White adipose tissue samples (abdominal fat pads) from wild type (WT) and obese (ObOb +/+) animals were used. Approximately equal aliquots (100±15 mg) of adipose tissue from several individual animals were prepared. Simultaneous sample homogenization and fractionation was carried in specialized individual single use 1.4 ml containers (FIG. 2) using alternating hydrostatic pressure generated in the BAROCYCLER® NEP-3229 (Pressure BioSciences, Inc., West Bridgewater, Mass.) for 20 cycles at room temperature. Each cycle consisted of 20 s at 35,000 psi followed by 20 s at atmospheric pressure. A protease inhibitor cocktail (Sigma-Aldrich, St. Louis, Mo.) was added to the extraction reagent in every case. Following the pressure cycling treatment, sample tubes were removed from the BAROCYCLER® and briefly centrifuged to promote complete separation of liquid phases. Unless otherwise noted, the top liquid layer from each tube was removed with a gel-loading pipette tip and stored for subsequent analysis of lipid fractions. Each polar fraction was desolvated in a SpeedVac centrifugal concentrator (ThermoFisher Scientific) to approximately 5-10 µl and reconstituted in either 2× Laemmli SDS-PAGE buffer (4% SDS) or in the 2D sample buffer (9M urea, 4% CHAPS) to provide compatibility with the desired downstream analysis method.

Adipose tissue: Lipid/Protein Fractionation Method. Alternating hydrostatic pressure was used to simultaneously homogenize the sample and promote partitioning of sample compounds between the immiscible liquid phases in a single disposable container. Extraction was performed in 1.2 mL of HFIP with 0.2 mL of mineral oil. The resulting extract was directly compatible with LC-MS/MS applications and electrophoretic separation of protein.

Control extraction directly in 2D sample buffer was conducted in two consecutive steps, 50 µl aliquots of each extraction were removed for protein assay and SDS-PAGE analysis, then extracts from the first and second round were combined, reduced, alkylated using TBP/acrylamide, and concentrated to the original sample volume in Amicon ULTRA-4 ultrafiltration devices (Millipore Corporation, Danvers, Mass.).

Electrophoresis, Image Analysis and in-Gel Digestion

SDS PAGE was performed on 4-12% polyacrylamide gradient gels. Immobilized pH Gradient strips pH 3-10 were hydrated with samples for 6 hours, followed by isoelectric focusing (IEF) for 100,000 Volt-hours at 10,000V. All pre-cast electrophoresis supplies and Criterion vertical gel electrophoresis system were from Bio-Rad Laboratories, Hercules, Calif., while the IsoelectrIQ2 integrated IEF instrument was from Proteome Systems, Woburn, Mass. Gels were stained with colloidal Coomassie Brilliant Blue (Proteome Systems) or SYPRO® Ruby (Bio-Rad Laboratories), scanned, and analyzed with PDQuest software to determine statistically significant differentially extracted proteins. Selected gel spots or bands were excised and processed using conventional in-gel digestion protocol. Sequencing grade modified porcine trypsin (Promega) has been used for digestion.

Protein Identification by Nano-Lc Fticr Tandem Mass Spectrometry

Protein digests (5-10 µL) were injected onto a C18 solid phase extraction trapping column (300 mm i.d.×5 mm, Dionex, Calif.) and 75 mm i.d.×15 cm nano-LC reversed-phase self-packed fused silica column (stationary phase: Magic C18AQ, 3 µm, 100 Å (Michrom Bioresources, Mass.); column: PicoFrit, 15 mm i.d. pulled tip through the 10-port Valco valve. Peptide separation was carried out using linear gradient of acetonitrile in 0.1% FA and the eluent was introduced into the LTQ FTICR mass spectrometer (Thermo Fisher Scientific) by nanoelectrospray. Data analysis has been conducted on the SORCERER™ (Sage-N) search engine using SEQUEST algorithm and GPMDB software. The search was performed against a combined "forward" and "reverse" FASTA DB. The balance between the reliability and sensitivity of protein identification data was set by adjusting the estimated false positive protein identification rate (FPPrR) to <1%. Duplicate peptide matches were purged on the basis of Xcorr to eliminate redundancy caused by homological proteins and isoforms. Similar proteins were listed with the protein entry of the highest score without adding redundancy into protein IDs lists of DTASelect and Protein Prophet outputs.

Results and Discussion

Experiments to remove lipid from membrane preparation that employed organic solvents and amphiphilic fluorinated alcohols have been carried out in series with cell disruption and fractionation by conventional methods. We have developed a detergent-free tissue dissolution and fractionation technique based on liquid-liquid extraction, enhanced by alternating hydrostatic pressure which promotes partitioning of analytes by transiently creating a metastable "hybrid" solvent at the interface between immiscible liquids. Pressure cycling instrumentation generates cycles of hydrostatic pressure which transiently alter the mutual solubility of immiscible solvents, resulting in a more efficient partitioning of sample constituents between liquid phases. In traditional extraction, high (e.g., up to 70% by weight) lipid content sequesters detergents into micelles, leaving the hydrophobic protein associated with the lipid mass.

Detergent-free extraction of protein from adipose tissue was performed. Upon depressurization, appropriately chosen liquid phases separate, carrying respective analytes according to their partitioning coefficients in corresponding solvents.

A comparison of different extraction reagents was performed. Protein recovery was quantified by determined by Bradford assay. The final volume of each extract was 1.4 ml.

Several combinations of organic solvents, both non-polar and amphiphilic, have been found along with aqueous buffers to promote liquid-liquid partitioning. The new method offers direct compatibility with downstream separation methods such as electrophoresis, chromatography and mass spectrometry. A remarkable difference in protein extraction efficiency has been demonstrated with various solvent systems. Two consecutive protein extractions from adipose tissue samples with IEF sample buffer (9M urea, 4% CHAPS) were performed and provide evidence of protein remaining in the mass of fat after the first extraction.

Simultaneous adipose tissue disruption, de-lipidation by hexane and extraction in 2× Laemmli sample buffer (4% SDS) or deionized water using pressure cycling was performed. While solvents such as hexane and benzyl alcohol allow delipidation of tissue concurrently with extraction by aqueous buffers, several polar solvents such as isopropanol allow fractionation of protein by their hydrophobicity in a stepwise extraction approach.

Addition of amphiphilic solvents, i.e., HFIP, to some solvent compositions leads to a nearly complete tissue dissolution and phase separation. Extraction of proteins from a 100 mg block of normal murine white adipose tissue was performed. Comparison of conventional 2D sample extraction buffer and a tissue dissolution approach by pressure cycling in a hexafluoroisopropanol-containing solvent system with subsequent removal of lipid fraction and solvent and reconstitution in the 2D electrophoresis sample buffer was performed. The CHAPS-based 2D electrophoresis buffer extracts predominantly blood plasma proteins, while the solvent-based extract contains a nearly complete protein complement of the adipose tissue. Examples are provided in Table 2.

TABLE 2

Example of adipose-specific protein perilipin frequently underrepresented in samples extracted by the conventional methods

| Protein ID | Charge_Peptide Sequence | nsp adj prob |
|---|---|---|
| lipid droplet-associated protein perilipin [Mus musculus] | 3_ILHLTPAQAVSSTK | 1 |
| gi\|26279005\|gb\|AAN77870.1\| | 2_EVTALPNPR | 1 |
| gi\|26327331\|dbj\|BAC27409.1\| | 3_IASELKGTISTR | 0.85 |
| gi\|28316726\|ref\|NP_783571.1\| | 2_LASGGADLALGSIEK | 1 |
| gi\|42559472\|sp\|Q8CGN5\| PLIN_MOUSE | 2_ILHLTPAQAVSSTK | 1 |
| Probability Score: 1.00 | 2_VSTLANTLSR | 0.95 |
| Sequence Coverage: 28.11% Number of Unique Peptide Matches: 7 | 2_ETAEYAANTR | 0.83 |

Several proteins have been found to be largely underrepresented in proteomic profiles of adipose tissue obtained using conventional extraction techniques. Detailed analysis of these proteins and their posttranslational modifications may provide crucial information on the regulation of fatty acid metabolism and possible ways to prevent the occurrence of Type II diabetes and obesity. For example, representative spectral interpretation of one of the several isoforms of murine FABP aP2 was performed. Diversity of the aP2 gene products could be explained by post-translational modifications, possibly possessing a regulatory role.

Example 8

Protein Recovery from HFIP; Solvent Removal by Evaporation Versus Precipitation with Distilled Water Pressure-assisted extraction and partitioning of polar and non-polar sample constituents results in formation of at least one liquid phase, a solution of the sample. In some cases, a multiplicity of liquid phases is formed. The phases may be physically separated by suitable techniques. Resulting individual phases are subjected to analysis by a number of possible methods—column chromatography, including HPLC; gel electrophoresis, e.g., SDS-PAGE or 2D-gel electrophoresis, etc.

In this example, sample constituents of interest are proteins. Moreover, the proteins are dissolved in an organic solvent. In certain cases, the solvent is a halogen-containing organic solvent, such as chlorinated alcohol, chlorinated acid, fluorinated alcohol, fluorinated acid, etc., or a mixture of thereof. Several of the halogen-containing organic solvents may act as detergents, in the sense that they cause changes to the protein conformation. In several examples, protein conformation in an organic solvent may be different than protein conformation in an aqueous solution. Protein solubility in the organic solvent can be modified by addition of a reagent such as an aqueous solution. As this example shows, the concentration of protein or other solute in the organic solvent may need to be above a certain threshold to induce efficient precipitation.

Example 8a 250 mg of bovine adipose tissue was processed by pressure cycling in 1 ml of HFIP. Pressure cycling conditions were as follows: 20 cycles of 20 seconds at 35 kpsi followed by 20 seconds at atmospheric pressure. PULSE tubes were used in the pressure cycling steps.

After pressure cycling, the sample was centrifuged at 11,000 g in order to promote phase separation into a lipid fraction and a protein fraction. The lower fraction (containing protein) was recovered and split into equal-sized aliqouts. One of the aliquots was evaporated to dryness in a centrifugal vacuum concentrator (SpeedVac, Thermo Scientific, Waltham, Mass.). The duplicate aliquot was precipitated by addition of distilled water (3 times the volume of the sample), chilled on ice for 10 minutes, and the pellet was recovered by centrifugation at 11,000 g for 15 minutes. The supernatant (water/HFIP mixture) was transferred to a clean tube and evaporated as described above to determine whether any proteins were lost during the precipitation.

All samples were reconstituted in SDS-PAGE sample buffer and run on a gel. The resulting gel was stained with Coomasie Blue to compare protein recovery by the two methods (data not shown). The gel results showed that under these conditions, the protein band pattern and intensity are comparable in the precipitated sample relative to the evaporated sample. In addition, the gel analysis confirmed that no detectable protein was present in the water/HFIP supernatant after precipitation, confirming that there was no detectable loss of protein during sample precipitation.

Example 8b

When bovine adipose tissue was processed as above, but the ratio of tissue mass to HFIP volume was reduced from 250 mg/ml to approx 40 mg/ml (corresponding to 50 mg of bovine adipose tissue processed by pressure cycling in 1.3 ml of HFIP), the precipitation reaction did not efficiently recover the dissolved protein, and much of the sample was observed to remain in the water/HFIP fraction.

Example 8c

When bovine adipose tissue was processed as above, but the ratio of tissue mass to HFIP volume was increased from approx 40 mg/ml, to 125 or 167 mg/ml by reducing the volume of HFIP (these ratios correspond to 50 mg tissue in 0.3-0.4 ml of HFIP), the precipitation reaction efficiency was restored. The samples were recovered in the precipitated pellet and no detectable protein was lost in the water/HFIP fraction. In order to displace the extra volume in the PULSE Tube, mineral oil was added to the reactions to bring the final total reaction volume up to 1.3-1.4 ml. The extra mineral oil had no noticeable effects, positive or negative, on the pressure cycling extraction or the precipitation reaction.

Example 8d

Similar experiments were performed with beef adipose tissue to examine different adipose tissue:HFIP ratios (mass: vol). The ratio was adjusted by changing the volume of mineral oil. The results showed that precipitation efficacy was improved at higher adipose tissue:HFIP ratios, e.g., ~160 mg/ml.

Example 9

Effects of Mineral Oil on Protein Extraction by Pressure Cycling

Example 9a

The addition of mineral oil to the pressure cycling reaction can be advantageous by improving phase separation, regardless of whether the sample is extracted from the solvent by drying or by precipitation. In addition, removal of the lipid phase may not be required prior to protein recovery by the precipitation method, if recovery of the lipid fraction is not intended (see, e.g., Example 10).

50 mg of porcine adipose tissue was processed by pressure cycling in 3 different combinations of HFIP/mineral oil (0 ml oil/1.3 ml HFIP; 0.1 ml oil/1.2 ml HFIP; or 0.5 ml oil/0.8 ml HFIP). Following pressure cycling (20 cycles of 20 sec at 35 kpsi followed by 20 sec at atmospheric pressure), the samples were centrifuged at 11,000 g in order to promote phase separation into a lipid fraction and a protein fraction. The lower fraction from each sample (containing protein) was transferred to a fresh test tube and evaporated to dryness in a centrifugal vacuum concentrator (SpeedVac, Thermo Scientific, Waltham, Mass.). All samples were reconstituted in SDS-PAGE sample buffer and run on a gel. The resulting gel was stained with Coomasie Blue to compare protein recovery and band sharpness (data not shown). The gel results indicated that under these conditions, the addition of mineral oil to the sample did promote some improvement in band sharpness and intensity. Increasing the amount of mineral oil from 0.1 to 0.5 ml per sample had no deleterious effects, and may actually have been beneficial, as the bands in the sample containing 0.5 ml of mineral oil were the most intense of the three samples tested. In summary, the addition of oil is not detrimental, and may be beneficial for phase separation and extraction efficiency.

Example 9b

The addition of mineral oil to the pressure cycling reaction can be advantageous by promoting phase separation in samples that do not normally separate into phases, such as brain tissue. 120-130 mg of rat brain tissue was extracted in 3 different combinations of HFIP/mineral oil (0 ml oil/1.1 ml HFIP; 0.1 ml oil/1.0 ml HFIP; or 0.5 ml oil/0.6 ml HFIP) and processed by pressure cycling at 20 cycles of 20 seconds at 35 kpsi and 20 seconds at atmospheric pressure. Duplicate samples were processed by drying and by precipitation. The gel results indicated that the addition of mineral oil and subsequent drying of the samples significantly improved band sharpness. Without the addition of mineral oil, the endogenous fats present in the sample were not efficiently removed and resulted in the formation of micelles that significantly interfered with band separation on SDS-PAGE gel. When mineral oil was added to the reaction (either 0.1 or 0.5 ml), the improved phase separation allowed for the efficient partitioning of the endogenous lipids into the oil layer during centrifugation. As a result, the gel electrophoresis results were dramatically improved. Addition of mineral oil to the samples that were subsequently precipitated also resulted in some improvement, although even in the absence of added oil, precipitated samples exhibited better band separation than dried samples.

Example 10

Alternative Solvent Removal Method: Results Comparable to Those Obtained Using Mineral Oil Under some circumstances, the same benefit of the addition of mineral oil may be achieved by switching from the drying protocol to the precipitation protocol. 120-130 mg of rat brain tissue was extracted in 2 different combinations of HFIP/mineral oil (0 ml oil/10.1 ml HFIP, 0.1 ml oil/10.0 ml HFIP) and processed by pressure cycling at 20 cycles of 20 seconds at 35 kpsi and 20 seconds at atmospheric pressure. After pressure cycling, the samples were centrifuged at 11,000 g in order to improve phase separation and the lower fraction (containing protein) was recovered and precipitated by the addition of distilled water (3 times the volume of the sample), chilled on ice for 10 minutes, and the pellet was recovered by centrifugation at 11000 g for 15 minutes. The samples were reconstituted in SDS-PAGE sample buffer and run on a gel. The resulting gel was stained with Coomasie Blue to compare protein recovery and band sharpness. The gel results indicate that under these conditions, there are no significant disadvantages of added oil. It is likely that under these precipitation conditions, endogenous lipids do not precipitate with the proteins and thus are not present in the sample during electrophoresis.

Example 11

Effects of Exogenous Salts

Exogenous salts can be added to improve total protein precipitation. In addition, optimized salt concentrations can be used to selectively precipitate desired proteins and retain undesired proteins in the supernatant. Four purified proteins-bovine serum albumin (Fraction V) (BSA), carbonic anhydrase, chicken egg white lysozyme, and human gamma-globulin (all obtained from Sigma-Aldrich, St. Louis, Mo.)—were dissolved in HFIP to a final concentration of 20 mg/ml. Individual proteins or a 1:1:1:1 mixture of all four proteins were precipitated with a three-fold excess volume of dH$_2$O, precipitated on ice for 20 minutes, and centrifuged for 15 minutes at 10,000 g. The pellets were reconstituted in SDS-PAGE sample buffer. The supernatant was also recovered, dried down in a SpeedVac, and resuspended in SDS-PAGE sample buffer. All resulting samples were run on a gel. The resulting gel was stained with colloidal Coomasie Blue.

Efficiency of protein precipitation with distilled water is protein-specific. While BSA and carbonic anhydrase efficiently precipitated and were recovered in a pellet, both lysozyme and gamma-globulin remained primarily in the supernatant.

Moreover, the mixture of the same proteins was fractionated by selective precipitation of some of the proteins by dH$_2$O, while others remained in solution. However, addition of 25 mg/ml NaCl solution instead of dH$_2$O improved the precipitation of the proteins that did not precipitate with water alone. This method can be applied to fractionate complex protein mixtures.

Example 12

A Detergent-Free Sample Preparation Technique for Concurrent Isolation and Fractionation of Protein, Nucleic Acids and Lipids from Biological Samples This method takes advantage of a synergistic combination of cell disruption by alternating hydrostatic pressure (Pressure Cycling Technology, or PCT) and a reagent system that dissolves and partitions distinct classes of molecules into separate fractions. PCT-assisted liquid-liquid extraction uses high hydrostatic pressure to alter solvation energy and solubility of various compounds. Several liquids, which are immiscible at atmospheric pressure, interact under high pressure in such a way that the phase boundary presents less of a barrier for partitioning of molecules between solvent phases. As a result, partitioning occurs in the entire volume of the vessel, rather then just at the interface. Proteins and lipids are solubilized under pressure and are maintained in solution by amphipathic organic solvents, such as fluorinated alcohols, e.g., hexafluoroisopropanol (HFIP). The new PCT/HFIP extraction method, provides efficient simultaneous extraction of proteins, lipids and nucleic acids from samples that are precious or unique, such as human or wild animal biopsy tissue or samples that are difficult to duplicate, such as small cell populations like early stem cell cultures. Another advantage of this method, is in more accurate analysis of non-homogenous samples. Because splitting samples for separate protein, lipid and nucleic acid analyses is not necessary, artifacts due to uneven distribution of components in the sample are avoided. The combination of sample disruption by PCT and extraction in HFIP relies on non-enzymatic and detergent-free dissolution and partitioning of sample components to efficiently and easily extract lipids, proteins, RNA and DNA from many types of samples without the need for multiple replicates, inconvenient and time-consuming tissue homogenization methods or extensive post-extraction clean-up. Thus, the novel method may help to enable unique systems biology studies, where correlation of transcription profiles with protein expression, analyses of post-translational protein modifications and tissue lipid composition were previously considered impractical due to the limited quantities of available material, or where variability between individual samples is too great to permit accurate comparison between replicates.

The new method is advantageous not only for small and precious samples, but also for larger samples where a single convenient method for purification of multiple components is desired. Since the PCT/HFIP protocol is easily scalable for large samples, it has many advantages over other currently available methods. HFIP can be used with sample-to-solvent ratios as high as 250-300 mg/mL, and possibly higher in some cases. Higher sample-to-solvent ratios are important when subsequent purification steps involve precipitation reactions, since these are always less efficient in more dilute solutions. After PCT/HFIP extraction of the bulk of the sample's proteins and lipids, the nucleic acid-enriched fraction can be brought up in a relatively small volume of reagent for subsequent RNA or DNA purification. This would allow for much more efficient extraction from large samples that contain little RNA and DNA (e.g., soil, yogurt, skin etc.).

Extraction by hydrostatic pressure in an amphipathic solvent such as HFIP, results in rapid cell disruption, dissolution of lipids and dissolution and denaturation of proteins. Nucleic acids do not remain in solution after depressurization and can be recovered from the insoluble fraction after sample extraction. In addition, due to the unique conditions that favor the extraction of more lipophilic proteins, several protein species uniquely extracted by the new method have been identified by in-gel tryptic digestion and LC-MS/MS. The lipids extracted by this new method can be subjected to direct analysis using MALDI-TOF mass spectrometry without additional cleanup and separation steps such as chromatography or enzymatic digestion.

Example 12a

Examination of Individual Fractions after Pressure-Mediated Extraction in HFIP (PCT/HFIP)

For RNA and protein distribution analysis, ~4×10$^7$ PC12 cells were washed once with PBS, suspended in 0.9 mL HFIP and transferred to a PULSE tube. Mineral oil (0.5 mL) was added to bring the final volume to 1.4 mL. Twenty pressure cycles were applied to each sample. Each pressure cycle consisted of 20 seconds at 35,000 psi, followed by 20 seconds at atmospheric pressure. After PCT, the entire sample was split evenly into 2 tubes for protein and RNA replicate samples and centrifuged for 15 minutes at ~12,000 g to separate phases. Following centrifugation, the non-polar top phase layers were removed. The interface layers were transferred to clean tubes, centrifuged briefly, and any carryover of solvent was aspirated off. The solvent phases were transferred to clean tubes and dried on a SpeedVac to remove solvent. The pellets were centrifuged briefly to facilitate aspiration of residual solvent. For protein visualization by SDS-PAGE, the pellet, interface and dried solvent fractions were dissolved in 1 mL Laemmli sample buffer with 50 mM DTT. For RNA isolation, 1 mL TRIZOL® reagent was added to each fraction and the standard TRIZOL® protocol for extraction of RNA from cells was followed.

For DNA distribution analysis, 200 mg of frozen mouse liver was extracted as described above with 1.0 mL HFIP and 250 µL mineral oil. Sample was split into equal replicates and phases were separated as described above. DNA was extracted from the pellet, interface and dried solvent fraction of one replicate using the Qiagen DNEASY® Blood and Tissue kit according to manufacturer's instructions for extraction of DNA from cells.

RNA and DNA recovery from the three fractions was compared by agarose gel electrophoresis. Proteins from all three fractions were separated by SDS-PAGE. The bulk of the protein was recovered from the soluble phase. Nucleic acid recovery quantified by Qubit assay confirmed that the pellet and interface together accounted for ~90% of both RNA and DNA.

Bovine adipose tissue was extracted by PCT/HFIP and separated into three fractions. The lipid fraction and the insoluble fraction were subsequently re-extracted to determine whether any additional proteins could be recovered. The re-extracted samples were visualized by SDS-PAGE and confirmed that while a small amount of additional protein can be recovered from the solid residue, no detectable protein could be recovered from the lipid phase. For protein re-extraction from the lipid phase, 350 mg of bovine adipose tissue was processed by PCT in 1.05 mL HFIP without mineral oil. After extraction and centrifugation, the solvent phase was removed, the lipid phase was transferred to a clean test tube, and the pellet and interface were pooled. The pellet/interface fraction and the lipid fraction were then re-extracted with fresh HFIP and centrifuged for 10 minutes at 12,000 g. The solvent was removed by evaporation under vacuum, and the resulting samples were dissolved in Laemmli sample buffer and subjected to SDS-PAGE.

The above experiments demonstrate the following: 1) There is no detectable extractable protein in the lipid layer. 2) The polar solvent phase contains the bulk of the sample proteins, and only traces of RNA and DNA. 3) The pellet and the interface both contain RNA and DNA with the pellet containing ~70% of recovered nucleic acids and the interface containing ~20% (the remaining ~10% can be recovered from the solvent phase after evaporation).

Example 12b

Most of the simple and efficient methods for extraction of genomic DNA from tissues rely upon extensive enzymatic digestion of proteins to release intact DNA. We demonstrate that after extraction of proteins from cells or tissue by PCT with HFIP, the nucleic acid fraction can be processed for DNA isolation and that high yields of intact genomic DNA can be recovered. After protein extraction from a sample of cultured mammalian cells, the solid fraction was processed for DNA isolation using the DNEASY® kit (Qiagen) and recovery was compared to a control aliquot of cells extracted directly with the DNEASY® kit. This method normally is not compatible with recovery of intact tissue proteins since the protocol calls for extensive Proteinase K digestion to obtain maximal DNA yield.

Equal aliquots of cultured mammalian cells were processed by pressure cycling in HFIP for extraction of protein and DNA. Twenty pressure cycles were applied to each sample using a BAROCYCLER® (model NEP3229 or NEP2320.). Each pressure cycle consisted of 20 seconds at high pressure (35,000 psi) followed by 20 seconds at low (atmospheric) pressure. Protein extract was dried, dissolved in IEF buffer and subjected to 2D PAGE. The pellet and any solid interface layer, containing the bulk of the sample's DNA and RNA, were then processed for nucleic acid extraction. Nucleic acid recovery was measured with a Qubit Fluorometer (Invitrogen), using the QUANT-IT™ dsDNA BR assay kit for quantification of DNA.

The results demonstrate that DNA can be easily extracted from the solid phase by a number of available reagents, again without the need for labor intensive sample homogenization. In addition, since the bulk of the proteins have already been extracted from the nucleic acid fraction the likelihood of DNA degradation during extraction is very low.

Frozen mouse liver (23 mg per sample) was processed as above. After centrifugation, the protein phase was dried and subjected to SDS-PAGE. DNA was extracted from the solid phase using the DNEASY® kit. Control tissue was digested with Proteinase K prior to DNA isolation with the DNEASY® kit according to manufacturer's instructions.

TABLE 3

DNA Recovery from Liver Tissue and Cell Culture

| Sample/Method | Total DNA recovery (µg) |
|---|---|
| 22 mg mouse liver/DNEASY ® alone | 21 |
| 22 mg mouse liver/PCT/HFIP followed by DNEASY ® | 6 |
| Cultured cells/DNEASY ® alone | 22 |
| Cultured cells/PCT/HFIP followed by DNEASY ® | 20 |

The combination of the PCT/HFIP method for cell disruption and protein extraction, together with the DNEASY® kit for DNA purification, resulted in very good simultaneous recovery of DNA and protein from cells. In addition, the same sequential protocol was successfully applied to protein and DNA extraction from liver tissue. The protein extracts were analyzed by 1D or 2D PAGE and confirmed that a broad range of proteins are recovered from the PCT/HFIP extract. DNA recovery from cell culture using the combined method was comparable to DNEASY® control with Proteinase K digestion, while DNA recovery from the tissue sample was about 30% of that obtained from the control (Table 3).

Example 12c

DNA Extraction by Pct/HFIP is Compatible with a Wide Range of Sample Sizes

Figure 4:
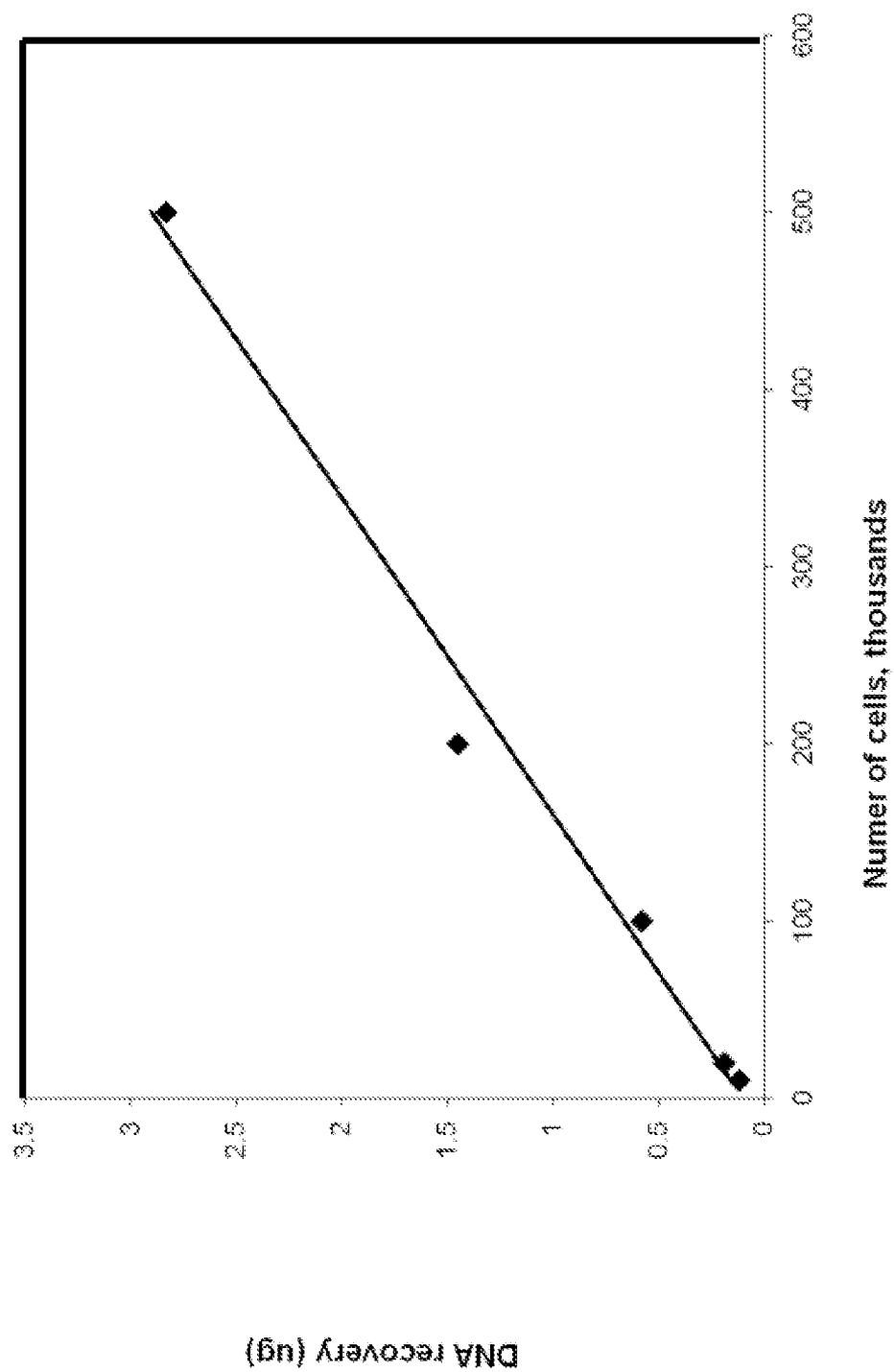
FIG. 4 is a line graph showing DNA recovery as a function of cell number in the methods described herein.

PC12 cells were pelleted by centrifugation, suspended in physiological buffer and counted. Aliquots of $1 \times 10^4$–$5 \times 10^5$ cells were extracted by PCT in 0.5-1.0 ml HFIP (final volume of each sample was adjusted to 1.4 mL by addition of mineral oil). After 20 cycles at 35 kpsi (20 seconds at high pressure, 20 seconds at atmospheric pressure), samples were transferred to centrifuge tubes and spun at ~12,000 g to separate phases and pellet the DNA-containing insoluble fraction. DNA was recovered from the pellet using the DNEASY® kit (Qiagen), DNA recovery as a function of cell number is shown in FIG. 4. The results confirm that DNA recovery by PCT/HFIP is efficient even from samples with as few as 10,000 cells.

Example 12d

Comparison of the PCT/HFIP Method with Other Commercially Available Methods for Simultaneous Extraction of RNA and Protein PC12 cells ($10^6$ cells per sample) were processed using PCT/HFIP, TRIZOL® Reagent from Invitrogen, the ALL-PREP™ RNA/Protein kit from Qiagen and the PARIS™ kit from Ambion.

For PCT/HFIP extraction, twenty pressure cycles were applied using a BAROCYCLER® (model NEP3229 or NEP2320). Each pressure cycle consisted of 20 seconds at high pressure (35,000 psi) followed by 20 seconds at low (atmospheric) pressure. After PCT extraction in HFIP, the protein-containing solvent phase was dried, dissolved in sample buffer and submitted to SDS-PAGE analysis. The pellet and solid interface layers were pooled and processed for RNA extraction by adding 0.5 mL of TRIZOL® and extracting by the standard TRIZOL® protocol. The other three samples were processed according to manufacturer's instructions. Equivalent aliquots of protein extract from each sample were separated by SDS-PAGE. Final volume of each RNA sample was 100 µL. Equal aliquots of each RNA sample were run on a gel to confirm that RNA was not degraded. The presence of prominent 28S and 18S ribosomal RNA bands on the agarose gels confirmed that the RNA extracted by all four methods was not degraded. Total RNA recovery was measured by the QUANT-IT™ RNA assay kit.

TRIZOL®, which is an optimized reagent designed primarily for RNA extraction, gave excellent RNA recovery, but the multi-step protocol for protein extraction and clean-up from the organic phase was slow, requiring two precipitation steps, three 30-minute washes in 300 mM Guanidine HCl in 95% ethanol and a final 20 minute wash in ethanol in order to remove the phenol and dye from the TRIZOL® reagent. This extensive clean-up may result in sub-stoichiometric in vitro protein modifications (N-termini, Lys), which could potentially interfere with downstream quantitative analysis of protein post-translational modifications. While the other three kits were easy to use, RNA recovery from the Ambion PARIS™ kit was consistently lower than with any of the other reagents (Table 4). This was likely due to the fact that after sample lysis, only half the lysate is used for RNA extraction, while the other half is reserved for protein. In addition, since at the end of the procedure the protein extract is still in the Cell Disruption buffer, which contains salts and detergent, additional protein clean-up steps, such as dialysis or filtration may be required. RNA recovery using the Qiagen kit was similar to that obtained with TRIZOL® and PCT/HFIP, but due to the low binding capacity of the columns, the sample (106 PC12 cells) had to be split onto 2 columns, increasing the amount of work and the cost of each sample. Also, due to the nature of the ALLPREP™ spin column used to separate the protein fraction from the RNA, many proteins remain with the bound RNA fraction and are absent from the recovered protein fraction. In addition, since the protein fraction collected by the ALLPREP™ protocol contains RNA stabilizing buffer, which is not compatible with SDS-PAGE, the proteins must to be acetone precipitated prior to SDS-PAGE analysis, which can lead to potential losses.

TABLE 4

Comparison of 4 reagents for simultaneous total RNA and protein recovery

| Method | Total RNA recovery from $10^6$ PC12 cells |
| --- | --- |
| PCT/HFIP | 11.9 µg |
| Ambion PARIS ™ kit | 5.3 µg |
| Qiagen ALLPREP ™ kit | 11.4 µg |
| TRIZOL ® | 16.2 µg |

Example 12e

To confirm that the RNA fraction recovered using the new method was not only intact, as indicated by the presence of 28S and 18S RNA on gels, but also contained intact mRNA and was compatible with RT-PCR, the four RNA samples described above, were subjected to real time-RT-PCR amplification using β-Actin primers. The RNA extracted from PC12 cells by PCT/HFIP compared very favorably with the three standard methods tested, indicating that the sample contains amplifiable mRNA at the expected concentration (Table 5).

TABLE 5

RT-RT-PCR quantification. Comparison of 4 reagents for simultaneous RNA and protein recovery

| Method | RNA recovery from $10^6$ PC12 cells. |
| --- | --- |
| PCT/HFIP | 16.4 µg |
| Ambion PARIS ™ kit | 9.0 µg |
| Qiagen ALLPREP ™ kit | 14.0 µg |
| TRIZOL ® (Invitrogen) | 14.0 µg |

Example 12f

In order to characterize the ability of the PCT-mediated liquid-liquid extraction method to delipidate and solubilize some hydrophobic proteins which are typically underrepresented in standard proteomic samples, we compared the extraction of murine white adipose tissue using two different extraction buffers followed by 2D-PAGE separation, in-gel digestion and analysis by LC-MS/MS. Replicate samples of murine abdominal fat were processed under similar conditions by pressure cycling using either the PCT/HFIP solvent system or detergent-based extraction buffer (7M urea, 2M thiourea, 4% CHAPS).

SDS-PAGE was performed on 4-12% polyacrylamide gradient gels. For 2D-PAGE separation, the simultaneous reduction and alkylation by tributylphosphine/acrylamide was employed. Immobilized pH Gradient strips pH 3-10 were hydrated with samples for 6 h, followed by IEF for 100,000 Volt-hours at 10,000V. All pre-cast electrophoresis supplies and Criterion vertical gel electrophoresis system were from Bio-Rad Laboratories (Hercules, Calif.), while the IsoelectrIQ$^2$ integrated IEF instrument was from Proteome Systems (Woburn, Mass.). Gels were stained with colloidal CBB or SYPRO® Ruby, scanned, and analyzed with PDQuest software to determine statistically significant differentially extracted proteins. Selected gel spots were excised and processed using a conventional in-gel digestion protocol [26]. Sequencing grade modified porcine trypsin (Promega, Madison, Wis.) was used for digestion.

Protein digests (5-10 µL) were separated using a $C_{18}$ solid phase extraction trapping column (300 µm i.d.×5 mm, Dionex, Calif.) and 100 µm i.d.×12 cm nano-LC reversed-phase self-packed fused silica column (PicoFrit, pulled tip of 8 µm i.d. (New Objective, Inc., Woburn Mass.), stationary phase: Magic C18AQ, 3 µm, 100 Å (Michrom Bioresources, Auburn, Calif.) using a linear gradient of acetonitrile in 0.1% formic acid. The eluate was introduced into either an LTQ Orbitrap or LCQ Deca XP Plus mass spectrometer (Thermo Fisher Scientific, San Jose, Calif.) by nanoelectrospray. Data analysis was conducted on the SORCERER™ (Sage-N Research, San Jose, Calif.) search engine using the SEQUEST-SORCERER™ algorithm. The search was performed against a concatenated "forward" and "reverse" FASTA database. Identification results were filtered and validated using Protein Prophet and Peptide Prophet platforms. The balance between the reliability and sensitivity of protein identification data was set by adjusting the estimated false positive identification rate to <1%.

Several proteins were identified on 2D gels of mouse adipose tissue extracted by PCT/HFIP which were absent or significantly less abundant in samples extracted with detergent. These include ferritin light chain, apolipoprotein A1, superoxide dismutase [Cu—Zn], perilipin (lipid droplet associated protein), alpha enolase and carbonic anhydrase.

Example 12g

Direct application of the lipid fractions derived from the pressure cycling-mediated hfip extraction are compatible with maldi-tof analysis using dhb matrix in positive ionization mode. Lipids were extracted from rat brain tissue by PCT using HFIP with mineral oil as described above. Beef pericardial fat was extracted by PCT/HFIP without added mineral oil. The lipid phases from both tissues were subjected to MALDI-TOF analysis.

The lipid fraction extracted by PCT/HFIP does not require further clean-up methods such as chromatography, additional extraction steps or enzymatic digestion, rather it can be used directly for analysis by MALDI-TOF mass spectrometry. Phospholipid and triglyceride profiling of lipid phase by MALDI-TOF were performed as described previously, with the following modifications: aliquots of lipid phase fraction (0.5 μL) were spotted directly onto a 2 μL droplet of 0.5 M 2,5-dihydroxy-benzoic acid (DHB) matrix solution in 50% acetonitrile/water immediately after droplet deposition onto the MALDI target. This method of sample application prevented spreading of the droplet across multiple spot locations of the MALDI target due to very low viscosity and surface tension of the lipid solution in organic solvent. Additionally, application of an amphipathic solvent onto the crystallizing matrix mixture resulted in formation of relatively uniform matrix/sample spots. Data were collected in positive ionization mode on an ABI 4700 Proteomics Analyzer (Applied Biosystems, Foster City, Calif.).

The results indicate that lipids extracted by the new method represent a broad range of lipid types and are sufficiently pure to be analyzed directly without additional purification steps. Tissue-specific lipid spectra were obtained from the two different tissues. Phospholipids characteristic of brain samples are apparent in the rat brain extract but absent from the lipid composition of the bovine adipose tissue.

Example 12h

To further demonstrate the utility of the PCT/HFIP extraction method, sequential extraction of protein, RNA and DNA from 5 different rat tissues was performed.

Flash frozen rat tissues (264 mg kidney, 330 mg abdominal fat pad, 310 mg liver, 264 mg brain, 200 mg cardiac muscle) were processed using 1.0 mL HFIP and 150-200 μL of mineral oil per sample. Twenty pressure cycles were applied to each sample using a BAROCYCLER® (model NEP3229 or NEP2320.). Each pressure cycle consisted of 20 seconds at high pressure (35,000 psi) followed by 20 seconds at low (atmospheric) pressure. After PCT and centrifugation, 10% aliquots of each protein fraction were prepared for SDS-PAGE. The pellet and interface fractions from each sample were pooled, dissolved in 0.5 mL TRIZOL®, vortexed thoroughly and processed according to the standard TRIZOL® protocol for extraction of RNA and DNA from cells.

The protein-containing fractions separated by SDS-PAGE revealed tissue-specific protein patterns in each of the samples. Agarose gel electrophoresis confirmed that the RNA was intact as indicated by the presence of 28S and 18S ribosomal RNA. Using the TRIZOL® protocol for isolation of RNA and DNA from the solid phase, we confirm that both genomic DNA and intact total RNA can be isolated after protein extraction by PCT/HFIP (Table 6).

The results confirm that PCT/HFIP-mediated tissue disruption and extraction allows for the efficient recovery of proteins, intact RNA and genomic DNA from a variety of tissues.

TABLE 6

RNA and DNA Recovery from Cells and Tissues

| Tissue | RNA recovery per mg tissue or $10^6$ cells | DNA recovery per mg tissue or $10^6$ cells |
| --- | --- | --- |
| Rat Liver | 2.40 μg | 34.5 ng (140 ng*) |
| Rat Kidney | 0.70 μg | 35.5 ng |
| Rat Adipose | 0.02 μg | 0.67 ng |
| Rat Brain | 0.55 μg | 37.08 ng |
| Rat Cardiac Muscle | 0.34 μg | 12.80 ng |
| PC12 cells | 11.90 μg | 10.70 μg* |

*PCT/HFIP protein extraction was usually followed by RNA and DNA isolation using TRIZOL ® reagent (or the DNEASY ® kit where indicated by *).

A number of embodiments of the invention have been described. Nevertheless, it will be understood that various modifications may be made without departing from the spirit and scope of the invention.

What is claimed is:

1. A pressure-assisted liquid-liquid method of extracting a component of interest from a plurality of components, the method comprising:
   providing a mixture that comprises a sample including a plurality of components and a fluorinated amphiphilic solvent, wherein the plurality of components comprises a component of interest, and wherein the mixture is free of surfactants and/or detergents; and
   subjecting the mixture to a pressure cycle to promote phase separation, the pressure cycle comprising:
      exposing the mixture to a first hydrostatic pressure;
      exposing the mixture to a second hydrostatic pressure to facilitate fractionation of the sample into the plurality of components, wherein the second hydrostatic pressure is greater than the first hydrostatic pressure; and
      reducing the pressure from the second hydrostatic pressure, resulting in the formation of at least two liquid phases from the solvent and the plurality of sample components whereby the component of interest is partitioned into one of the at least two liquid phases to extract the component of interest from the plurality of components.

2. The method of claim 1, wherein the component of interest is at least one protein, lipid, nucleic acid, or small molecule.

3. The method of claim 1, wherein the plurality of components is partitioned into a liquid phase that is substantially free of the component of interest.

4. The method of claim 1, further comprising isolating the component of interest from the liquid phase.

5. The method of claim 1, wherein the extracted component of interest is directly compatible with a downstream process.

6. The method of claim 1, wherein the plurality of components is of biological origin.

7. The method of claim 6, wherein the plurality of components of biological origin is from an animal, fungus, bacterium, virus, or plant.

8. The method of claim 1, wherein the second pressure is reduced to a third pressure, and wherein the first, second, and third hydrostatic pressures comprise the pressure cycle.

9. The method of claim 8, wherein the mixture is exposed to repeated pressure cycles.

10. The method of claim 9, wherein the mixture is exposed to between about 1 and about 1000 pressure cycles.

11. The method of claim 10, wherein the third hydrostatic pressure is less than the first hydrostatic pressure.

12. The method of claim 10, wherein the third hydrostatic pressure is equal to the first hydrostatic pressure.

13. The method of claim 10, wherein the third hydrostatic pressure is greater than the first hydrostatic pressure.

14. The method of claim 1, wherein the first hydrostatic pressure is between about 0.1 MPa to about 1,000 MPa.

15. The method of claim 1, wherein the component of interest is a nucleic acid, a bacterium, a pesticide, a polysaccharide, a polyphenol, a vitamin, a toxin, a pollutant, a lipid, a glycolipid, a steroid, a membrane, a component of interest in a bacterial inclusion body, an antigen, a virus, a pharmaceutical agent, a metabolite, a drug, a drug metabolite, a dye, a food constituent, a nanoparticle formulation, a lipid raft, an amyloid plaque, microtubule, cytosol, or a particular cell type.

16. The method of claim 1, wherein a plurality of components of interest are extracted from the plurality of components.

17. The method of claim 16, wherein the plurality of components of interest comprises a nucleic acid and a protein.

18. The method of claim 1, wherein the plurality of components provides a liquid phase or a plurality of liquid phases.

19. The method of claim 18, wherein the liquid phase is a lipid, an organic solvent, an aqueous buffer, an emulsion, or a suspension of solid particles.

20. The method of claim 18, wherein the liquid phase is formed from a solid phase under hydrostatic pressure.

21. The method of claim 14, wherein the second hydrostatic pressure is between about 100 kPa and about 1,000 MPa.

22. The method of claim 1, wherein the difference in pressure between the first and second hydrostatic pressures is between about 10 kPa and 1 GPa.

23. The method of claim 1, wherein the fluorinated amphiphilic solvent comprises HFIP, TFE, PFOA, Trifluoroacetic acid or other halogenated alcohol or acid.

24. The method of claim 1, wherein extracting the component of interest from the plurality of components comprises promoting separation of lipophilic and hydrophilic compounds into two or more liquid phases which can be subsequently mechanically separated.

\* \* \* \* \*